US008636172B2

(12) United States Patent
Dunn

(10) Patent No.: US 8,636,172 B2
(45) Date of Patent: Jan. 28, 2014

(54) DEVICES, SYSTEMS AND METHODS FOR POINT-OF-USE MEDICATION CONTROL

(76) Inventor: Lawrence A. Dunn, Durham, NC (US)

( * ) Notice: Subject to any disclaimer, the term of this patent is extended or adjusted under 35 U.S.C. 154(b) by 239 days.

(21) Appl. No.: 13/022,354

(22) Filed: Feb. 7, 2011

(65) Prior Publication Data

US 2011/0166700 A1    Jul. 7, 2011

Related U.S. Application Data

(63) Continuation-in-part of application No. 11/649,471, filed on Jan. 4, 2007, now Pat. No. 7,885,725.

(60) Provisional application No. 60/756,372, filed on Jan. 5, 2006.

(51) Int. Cl.
*B65H 3/00* (2006.01)

(52) U.S. Cl.
USPC ........... 221/261; 221/262; 221/263; 221/224; 221/151

(58) Field of Classification Search
USPC .................. 221/261, 151, 263, 262, 224, 268
See application file for complete search history.

(56) References Cited

U.S. PATENT DOCUMENTS

| | | | |
|---|---|---|---|
| 4,695,954 A | 9/1987 | Rose et al. | |
| 4,698,954 A | 10/1987 | Behr et al. | |
| 4,744,492 A | 5/1988 | Hackmann et al. | |
| 5,047,948 A | 9/1991 | Turner | |
| 5,127,543 A * | 7/1992 | Meisels | 221/266 |
| 5,329,459 A | 7/1994 | Kaufman et al. | |
| 5,408,443 A | 4/1995 | Weinberger | |
| 5,480,062 A | 1/1996 | Rogers | |
| 5,571,258 A | 11/1996 | Pearson | |
| 5,582,323 A | 12/1996 | Kurtenbach | |
| 5,646,912 A | 7/1997 | Cousin | |
| 5,657,236 A | 8/1997 | Conkright | |
| RE35,743 E | 3/1998 | Pearson | |
| 5,745,366 A | 4/1998 | Higham et al. | |

(Continued)

FOREIGN PATENT DOCUMENTS

WO   WO 2012/109222   8/2012

OTHER PUBLICATIONS

"Monitored Automatic Medication Dispenser MD.2 from e-pill," http://www.age-in-place.com/md2.html (Downloaded from the Internet on Nov. 17, 2005).

(Continued)

*Primary Examiner* — Timothy Waggoner
(74) *Attorney, Agent, or Firm* — Jenkins, Wilson, Taylor & Hunt, P.A.

(57) ABSTRACT

Devices, systems and methods for controlling dispensing of medication are provided. A dispenser device used, for example, in the systems and methods can include a housing for storing units of medication and a dispensing well having an opening therein to permit removal of units of medication therefrom. The dispenser device can include first and second slides having openings therein that are configured to funnel a unit of medication toward the opening in the dispensing well. The opening in the first slide can be configured to funnel a unit of medication to the opening of the second slide upon movement of the first slide, while the second slide can be configured to funnel the unit of medication to the opening in the dispensing well upon movement of the second slide into a position that is aligned with the opening in the dispensing well.

55 Claims, 36 Drawing Sheets

(56) References Cited

U.S. PATENT DOCUMENTS

| | | | |
|---|---|---|---|
| 5,905,653 A | 5/1999 | Higham et al. | |
| 5,971,594 A | 10/1999 | Sahai et al. | |
| 5,993,046 A | 11/1999 | McGrady | |
| 6,011,999 A | 1/2000 | Holmes | |
| 6,332,100 B1 | 12/2001 | Sahai et al. | |
| 6,431,399 B2 * | 8/2002 | Gabel et al. | 221/263 |
| 6,471,087 B1 | 10/2002 | Shusterman | |
| 6,594,549 B2 | 7/2003 | Spiegel | |
| 6,607,094 B2 | 8/2003 | MacDonald | |
| 6,650,964 B2 | 11/2003 | Spano, Jr. et al. | |
| 6,732,884 B2 | 5/2004 | Topliffe | |
| 6,736,286 B2 * | 5/2004 | Hashimoto et al. | 221/266 |
| 6,961,285 B2 | 11/2005 | Niemiec et al. | |
| 6,962,274 B1 * | 11/2005 | Sherman | 222/361 |
| 7,080,755 B2 | 7/2006 | Handfield | |
| 7,097,068 B2 * | 8/2006 | Limback et al. | 221/258 |
| 7,139,639 B2 | 11/2006 | Broussard et al. | |
| 7,418,311 B1 | 8/2008 | Lagassey et al. | |
| 7,753,229 B2 | 7/2010 | Hutchinson et al. | |
| 7,831,336 B2 | 11/2010 | Gumpert | |
| 7,885,725 B2 | 2/2011 | Dunn | |
| 7,886,931 B2 | 2/2011 | Handfield | |
| 8,032,252 B2 | 10/2011 | Berg | |
| 8,326,455 B2 | 12/2012 | Dunn | |
| 2007/0156282 A1 | 7/2007 | Dunn | |
| 2009/0308884 A1 | 12/2009 | Coughlin et al. | |
| 2011/0125317 A1 | 5/2011 | Dunn | |

OTHER PUBLICATIONS

"e-pill Multi-Alarm: Easy-to-Program Medication Reminder," http://www.age-in-Place.com/multialarm.html (Downloaded from the internet on Nov. 17, 2005).
"Automatic Pill Dispenser: e-pill Med-Time 'Electronic Pill Box' Automatic Medication Dispenser & Reminder," http://www.age-in-place.com/medtime.html (Downloaded from the internet on Nov. 17, 2005).
"MD.2 Personal Medication System," Interactive Medical Developments, L.C., http://www.imd2.com (Downloaded from the Internet on Nov. 17, 2005).
"Pyxis Corporation's Positive ID Assures Secure Access to Medications," Cardinal Health,http://www.cardinal.com/content/news/060198_65988.asp (Downloaded from the internet on Nov. 17, 2005).
"Hendricks Regional Health Adds State-of-theArt Medication-Use Technology to Increase Patient Safety," Omnicell, http://www.omnicell.com/news_events/release_display.asp?page=238 (Downloaded from the internet on Nov. 17, 2005).
"Fingerprint Sensors Enhance Accuracy in User-Authentication Application," Medical Devicelink, http://www.devicelink.com/emdm/archive/03/11/006.html (Downloaded from the internet on Nov. 18, 2005).
"Authentec: The Power of Touch—Electronic Fingerprint Sensor," Authentec main website, http://www.authentec.com (downloaded from the internet on Nov. 18, 2005).
Brian Robinson, "VA Improves Telehealth Access: Slimmer Equipment, Web Access Make a Better Case for Home Care," Technology Briefing (Jan. 6, 2002).
e-pill® website pages, http://www.epill.com/ (downloaded from the internet between Apr. 24, 2012 and May 1, 2012).
MedMinder™ website pages, http://www.medminder.com/ (downloaded from the internet on Apr. 13, 2012).
MedSignals website pages, http://www.medsignals.com/ (downloaded from the internet on Apr. 24, 2012).
TabSafe website pages, http://www.tabsafe.com/ (downloaded from the internet on Apr. 24, 2012).
Vitality™ wesite pages, http://www.vitality.net/index.html (downloaded from the internet on Apr. 13, 2012).
e-pill® product materials and brochures, (downloaded from the internet on May 1, 2012).
MedCenter™ "Recording your Minder, The Talking Personal Recording Alarm Clock", (downloaded from the internet on May 1, 2012).
Timex Healthcare Medication Manager Instruction Manual, (downloaded from the internet on May 1, 2012).
CASIO® User's Guide TMR-200, (downloaded from the internet on May 1, 2012).
Interactive Medical Developments, L.C., "MD.2 Users Manual", Dec. 1, 2005.
Notification Concerning Availability of the Publication Serial No. PCT/US2012/024118 dated Aug. 16, 2012.
International Search Report and Written Opinion for Application Serial No. PCT/US2012/024118 dated Aug. 24, 2012.
Non-Final Office Action for U.S. Appl. No. 12/953,754 dated Oct. 20, 2011.
Notice of Allowance and Fees for U.S. Appl. No. 12/953,754 dated Aug. 13, 2012.
Non-Final Office Action for U.S. Appl. No. 12/953,738 dated Aug. 24, 2012.
Non-Final Office Action for U.S. Appl. No. 11/649,471, dated Nov. 30, 2009.
Final Office Action for U.S. Appl. No. 11/649,471, dated May 19, 2010.
Notice of Allowance for U.S. Appl. No. 11/649,471, dated Sep. 30, 2010.
Notice of Allowance for U.S. Appl. No. 12/953,754, dated Apr. 30, 2012.
Final Office Action for U.S. Appl. No. 12/953,738, dated Mar. 15, 2013.

* cited by examiner

| _rowid | CLINICI | FIRST_NAME | LAST_NAME | PATIENT_ID |
|---|---|---|---|---|
| 1 | 1 | Karl | Richter | 1 |
| 2 | 1 | Donn | Smith | 3 |
| 3 | 1 | Peter | Omalley | 2 |
| 4 | 2 | Chelsea | Morn | 4 |
| 5 | 2 | Susan | Ormond | 5 |
| 6 | 2 | Renee | Tolefson | 6 |
| 8 | 3 | Ruth | Morgan | 8 |
| 18 | 4 | Willy | Wonka | 18 |
| 19 | 4 | Henry | Higgins | 19 |
| 20 | 4 | Ricky | Martin | 20 |
| 21 | 4 | Mary | Decker | 21 |
| 22 | 5 | Patty | Duke | 22 |
| 23 | 1 | K's first | patient | 23 |

Dose Tracker Direct:

Providing safety, compliance, and continuity for pharmacotherapy.

Username: _____
Password: _____
Assistant: ☐

[ Login ]

FIG.14

Dose Tracker Direct:

Providing safety, compliance, and continuity for medication.

Entities:
[Clinician ⇅]
[Search...]
[New...]

[Home]
[Logout]

Find
Entities:

| | | | | | |
|---|---|---|---|---|---|
| Clinician | where | [lastName ⇅] | is | [= ⇅] | [____] 🔍 |
| Patient | where | [lastName ⇅] | is | [= ⇅] | [____] 🔍 |
| Script | where | [medication ⇅] | is | [= ⇅] | [____] 🔍 |
| Tracker | where | [trackerNumber ⇅] | is | [= ⇅] | [____] 🔍 |

FIG.15

Dose Tracker Direct:
Providing safety, compliance, and continuity for medication.

Entities:
[Clinician ▼]
[Search...]
[New...]
―――――
[Home]
[Logout]

List
6 Clinicians

| | First Name ▲ | Last Name ≡ | Patient ID ≡ | |
|---|---|---|---|---|
| ✎ | Alphonse | Kildare | | 🗑 |
| ✎ | Parker | Peter | | 🗑 |
| ✎ | Paul | Oddom | | 🗑 |
| ✎ | Peter | Parker | | 🗑 |
| ✎ | Ross | Simmons | | 🗑 |
| ✎ | William | Osler | | 🗑 |

[Return]

FIG.16

Dose Tracker Direct:
Providing safety, compliance, and continuity for medication.

Entities:
[Clinician ▼]
[Search...]
[New...]
―――――
[Home]
[Logout]

Edit
Clinician

First Name [Alphonse]
Last Name [Kildare]
Patient ID [ ]
Patient [7, Zhivago, Yuri
        7, Martin, Cecil    ✎
        7, Najinsky, Dimitri]

[Cancel] [Delete] [Save]

FIG.17

Dose Tracker Direct:
Providing safety, compliance, and continuity for medication.

Entities:
[Patient ⇕]
[Search...]
[New...]
—
[Home]
[Logout]

List
32 Patients    Display [10] items                    ◀ Page [1] of 4 ▶

First Name ⬍ Last Name ≡

| | First Name | Last Name | |
|---|---|---|---|
| ✎ | | | 🗑 |
| ✎ | | | 🗑 |
| ✎ | | | 🗑 |
| ✎ | | | 🗑 |
| ✎ | Adrian | Andover | 🗑 |
| ✎ | Cecil | Martin | 🗑 |
| ✎ | Chelsea | Morn | 🗑 |
| ✎ | Cindy | Felen | 🗑 |
| ✎ | Dimitri | Najinsky | 🗑 |
| ✎ | Donn | Smith | 🗑 |

[Return]

FIG.18

Dose Tracker Direct:

Providing safety, compliance, and continuity for medication.

Entities:
[Patient ▾]
[Search...]
[New...]

[Home]
[Logout]

Edit
─────────────────────────────
Patient
  Clinician  Olser, William ✎
  First Name [Adrian]
  Last Name [Andover]
    Tracker  <com.webobjects.eocontrol.EOGenericRecord_ed053a_EOIntegral ✎

[Cancel] [Delete] [Save]

FIG.19

Dose Tracker Direct:

Providing safety, compliance, and continuity for medication.

Entities:
[Script ▾]
[Search...]
[New...]

[Home]
[Logout]

List
─────────────────────────────
3 Scripts

| | Days LENGTH ≡ | Dose ≡ | Interval ≡ | Medication ≡ | Strength ≡ | Tracker ID ≡ | |
|---|---|---|---|---|---|---|---|
| ✎ | 14 | 1 | 12 | Oxycontin | 20 | 2 | 🗄 |
| ✎ | 30 | 2 | 4 | Oxycontin | 40 | 1 | 🗄 |
| ✎ | 30 | 1 | 24 | Avinza | 100 | 3 | 🗄 |

[Return]

FIG.20

Dose Tracker Direct:

Providing safety, compliance, and continuity for medication.

Entities:

[Script ⇕]

[Search...]

[New...]

[Home]

[Logout]

Edit
_____

Script

Days Length [14]
Dose [1]
Interval [12]
Medication [Oxycontin]
Strength [20]
Tracker ID [2]

[Cancel] [Delete] [Save]

FIG.21

Dose Tracker Direct:

Providing safety, compliance, and continuity for medication.

Entities: [Tracker ▲▼]
[Search...]
[New...]

List
3 Trackers

| Contact Time | Latitude | Longitude | Patient ID | Pills Remaining | Postition Time | Script ID | Tracker Number |
|---|---|---|---|---|---|---|---|
| ✍ Feb 12,2005 | 234231 | 170334 | 1 | 17 | Feb 12,2005 | 1 | 1 |
| ✍ Feb 12,2005 | 273453 | 340713 | 2 | 34 | Feb 12,2005 | 2 | 2 |
| ✍ Feb 12,2005 | 1123421 | 341256 | 3 | 87 | Feb 12,2005 | 3 | 3 |

[Home]
[Logout]

[Return]

FIG.22

Dose Tracker Direct:

Providing safety, compliance, and continuity for medication.

Entities:

[Tracker ⇕]  Edit

[Search...]  Tracker

[New...]

Contact Time [Feb 12, 2005]  *Format: Apr DD, YYYY*
                  Latitude [234231]

[Home]
                Longitude [170334]
                Patient ID [1]

[Logout]
          Pills Remaining [17]
            Position Time [Feb 12, 2005]  *Format: Apr DD, YYYY*

Script 1, 30, 4, 2, 40, Oxycontin ✏

Script ID [1]
       Tracker Number [1]

[Cancel] [Delete] [Save]

FIG. 23

DEVICES, SYSTEMS AND METHODS FOR POINT-OF-USE MEDICATION CONTROL

RELATED APPLICATION

This application is a Continuation-in-Part of and claims priority to U.S. patent application Ser. No. 11/649,471 filed Jan. 4, 2007 and set to issue on Feb. 8, 2011 as U.S. Pat. No. 7,885,725, which claims the benefit of U.S. Provisional Patent Application Ser. No. 60/756,372, filed Jan. 5, 2006, the entire contents of which are both hereby incorporated by reference herein.

TECHNICAL FIELD

The subject matter described herein relates generally to systems and methods for medication compliance. More particular, the subject matter disclosed herein relates to devices, systems and methods for dispensing medication to an intended patient at predetermined and appropriate times in an outpatient setting to increase the likelihood of proper medication management of a patient after leaving the direct care of a doctor or health provider/professional.

BACKGROUND

The rate of compliance with medication regimens in outpatient settings is generally regarded as poor. Even under the watchful eye of doctors, studies have shown that trained professionals working in a controlled setting make significant errors in the delivery of medication to patients. Compliance with such medication regimens have been shown to be worse after a patient leaves a hospital and the medication management is required to be performed by the patient or some other untrained family member. For example, studies have shown that patients directed to take a single medication once per day have only succeeded about 70% of the time. Studies have further shown that, when three doses per day are required, compliance with such medication regimens falls to about 50%. Further, such studies show that compliance and compliance failures for such medication regimens do not correlate with social, economic, or educational variables.

Failure to comply with medication regimens prescribed by doctors can have severe consequences. For example, in the outpatient setting, a patient's recovery can be slowed and progress toward recovery can be minimized by the patient's failure to follow the prescribed medication regimen provided by a trained professional. Such lack of compliance can help in the development of drug resistant strains of bacteria and viruses. For example, tuberculosis has developed certain drug resistant strains in Africa due to the fact that rural patients have begun lengthy medication regimens that required multiple doses but fail to follow through and complete these regimens. Thereby, the tuberculosis has been allowed to persist in a form that has become resistant to the treatment being used. Such drug resistance strains could be minimized if the patients were able to properly follow through with their medication regimens.

A further concern applies to certain classes of medication that are prone to abuse. For example, certain narcotics and anxiety reducing medications are known to be addictive. For such medications, a patient will often begin to take increasing amounts of the medication at more frequent intervals that do not comply with the prescribed regimen set forth for the use of the drug. The controlling of dosing for these medications in the outpatient setting is so notoriously difficult that many physicians have simply begun to refuse to prescribe them.

Concerns about the diversion of a medication from the patient to other individuals have reduced the outpatient prescription of such drugs. For example, medications such as Oxycontin have addictive qualities and also have street value as a recreational drug. Often, people who are prescribed such a drug end up selling it to users who consume it recreationally. This concern is so great for Oxycontin that some state legislatures have considered banning its use.

In the examples provided above, drugs that were once valuable to society have lost part of their effectiveness through their misuse in one way or another. Therefore, in light of the above, a need exists for a system that allows outpatient medication to be dispensed in a secured, controlled, and monitored fashion to more effectively manage and organize the care given to a patient.

SUMMARY

In accordance with this disclosure, novel devices, systems and methods for point-of-use medication control in outpatient settings are provided.

The present disclosure provides devices, systems and methods for point-of-use medication control that can employ single dose distribution and dispensing at predetermined and appropriate times through patient awareness and identification as well as through compliance confirmation. This and other purposes as may become apparent from the present disclosure can be achieved, in whole or in part, by the presently disclosed subject matter when taken in connection with the accompanying drawings as best described herein below.

BRIEF DESCRIPTION OF THE DRAWINGS

A full and enabling disclosure of the present subject matter including the best mode thereof to one of ordinary skill in the art is set forth more particularly in the remainder of the specification, including references to the accompanying figures in which:

FIG. 8 illustrates a screen of a database that employs the data tables of FIG. 6;

FIG. 9 illustrates a screen of a database that employs the data tables of FIG. 6;

FIG. 10 illustrates a screen of a database that employs the data tables of FIG. 6;

FIG. 11 illustrates a screen of a database that employs the data tables of FIG. 6;

FIG. 12 illustrates a screen of a database that employs the data tables of FIG. 6;

FIG. 14 illustrates an interactive screen display window used for an internet web browser interface for a database of an embodiment of a system for a point-of-use medication control according to the present subject matter;

FIG. 15 illustrates an interactive screen display window used for an internet web browser interface for a database of an embodiment of a system for a point-of-use medication control according to the present subject matter;

FIG. 16 illustrates an interactive screen display window used for an Internet web browser interface for a database of an embodiment of a system for a point-of-use medication control according to the present subject matter;

FIG. 17 illustrates an interactive screen display window used for an internet web browser interface for a database of an embodiment of a system for a point-of-use medication control according to the present subject matter;

FIG. 18 illustrates an interactive screen display window used for an internet web browser interface for a database of an embodiment of a system for a point-of-use medication control according to the present subject matter;

FIG. 19 illustrates an interactive screen display window used for an internet web browser interface for a database of an embodiment of a system for a point-of-use medication control according to the present subject matter;

FIG. 20 illustrates an interactive screen display window used for an internet web browser interface for a database of an embodiment of a system for a point-of-use medication control according to the present subject matter;

FIG. 21 illustrates an interactive screen display window used for an internet web browser interface for a database of an embodiment of a system for a point-of-use medication control according to the present subject matter;

FIG. 22 illustrates an interactive screen display window used for an internet web browser interface for a database of an embodiment of a system for a point-of-use medication control according to the present subject matter;

FIG. 23 illustrates an interactive screen display window used for an internet web browser interface for a database of an embodiment of a system for a point-of-use medication control according to the present subject matter;

DETAILED DESCRIPTION

Reference will now be made in detail to presently preferred embodiments of the present subject matter, one or more examples of which are shown in the figures. Each example is provided to explain the subject matter and not as a limitation. In fact, features illustrated or described as part of one embodiment can be used in another embodiment to yield still another embodiment. It is intended that the present subject matter cover such modifications and variations.

Figure 1:
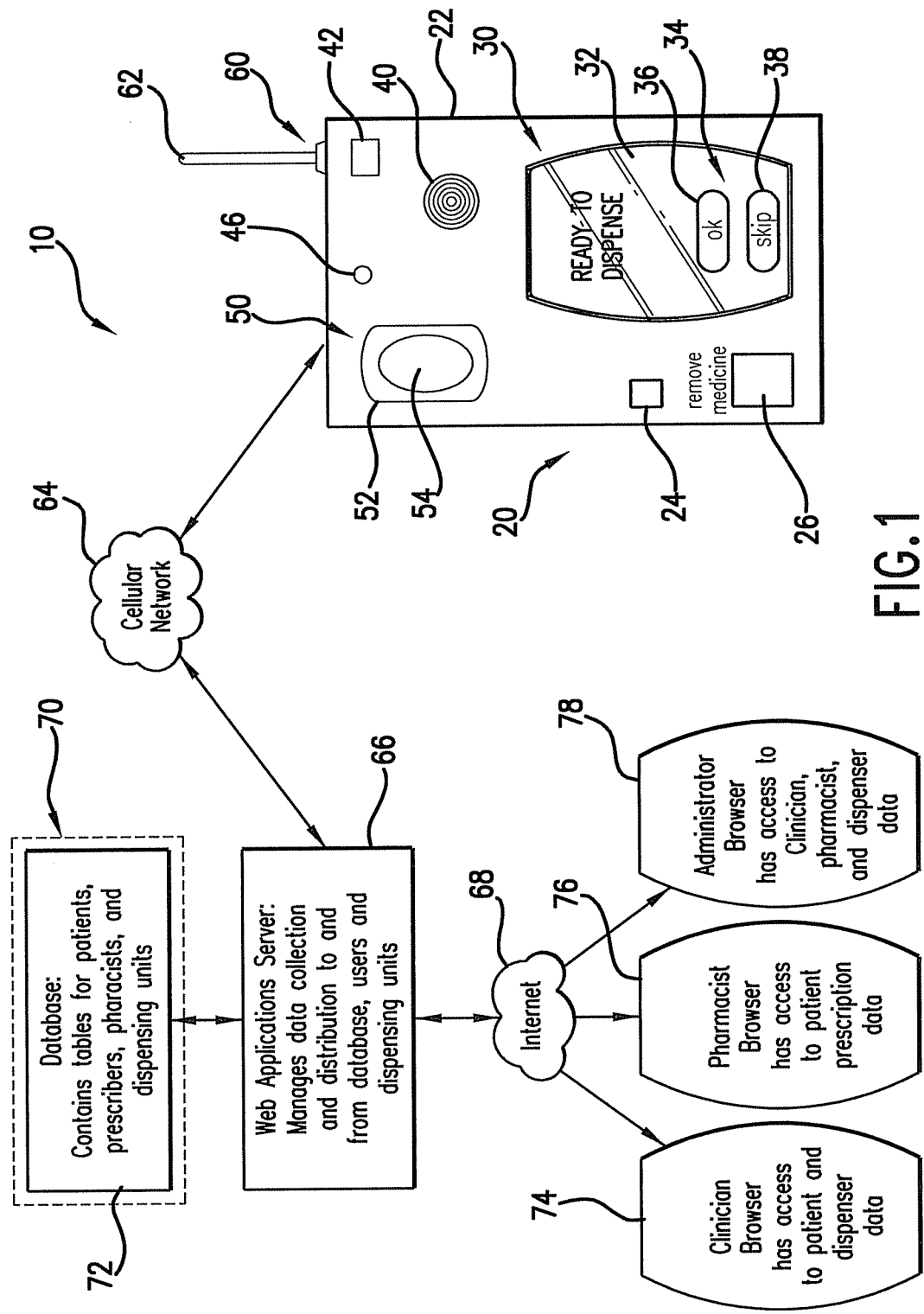
FIG. 1 illustrates a schematic of an embodiment of a system for a point-of-use medication control according to the present subject matter.

FIG. 1 illustrates a medication dispensation control system, generally designated as 10. System 10 can comprise a dispenser, generally designated as 20, that is capable of holding and delivering at least one dose of medication to a patient in an outpatient setting. Dispenser 20 can have an outer housing 22 that can enclose the operational components of a portion of system 10 within dispenser 20 and can prevent tampering and unauthorized removal of medication from dispenser 20. In use, dispenser 20 could be used to distribute units of medications in the form of tablets, pills or capsules at predetermined times to specified and identified individuals.

System 10 can also can comprise a controller, generally designated as 30. Dispenser housing 22 can enclose controller 30, which is operably connected to operable components of dispenser 20. Controller 30 can automatically operate dispenser 20 to provide a dose of medication to the patient at the appropriate or predetermined time. For example, controller 30 can be programmable with a medication dispensing program which can comprise a data store comprising the predetermined time to operate dispenser 20 and the name of the at least one medication. The data store of the medication dispensing program can also comprise patient data and a patient compliance schedule. Patient data can comprise the first and last name of the patient, the age of the patient, medical history information, or the like. Biometric information, such as fingerprint data or the like can also be considered patient data.

The data store of the medication dispensing program on controller 30 can also comprise caregiver data. The caregiver can be anyone such as a family member or nurse who is charged with taking care of the patient. In such cases where a caregiver is necessary to administer the medication to the patient, the caregiver can be allowed to engage system 10 to receive the medication to be administered to the patient. Caregiver data can comprise first and last name of the caregiver, contact information of the caregiver, or the like. Biometric information, such as fingerprint data or the like can also be considered caregiver data. Through such information, the caregiver can gain access to the medication to be administered to the patient.

The data store of the medication dispensing program on controller 30 can also comprise compliance notification data. Compliance notification data can comprise the frequency of timely compliance by the patient, data on the dates and times at which compliance occurs, or the like. The data store of the medication dispensing program on controller 30 can further comprise pharmacy data, physician data, insurance data and emergency contact data.

Controller 30 can comprise devices that emit any suitable type of signal to indicate dispenser 20 is ready to provide a dose of medication for the patient to receive. For example, a display screen, such as an interactive user interface display screen 32 can be provided that can alert the patient that a dose of medication is ready to be dispensed. In the embodiment shown in FIG. 1, a simple display indicating that the dispenser is ready to dispense is shown on display screen 32. The display also shows a user interface 34 on display screen 32 with which the patient can interact to acknowledge receipt of the signal. The user interface 34 can be a response button 36 in the form of a graphic display button that the user activates by touching the screen at the display location of the graphic display button. By activating this button 36, the patient acknowledges receipt of the signal and dispensing can begin. Other response mechanisms can be provided, including for example other graphic display buttons. For example, button 38 can be provided that allows the patient to skip the dispensing of the dose of medication.

Besides the display 32, a speaker 40 can be provided to provide an audible signal that would be emitted by the speaker 40. Speaker 40 can be internally contained with outer housing 22 or it can be external. In this manner, a patient who cannot view display 32 can still be notified of the availability of the dose medication. Once the patient has acknowledged receipt, then the audible signal can end as well. Other response mechanisms can be provided to allow the user to acknowledge receipt of the signal that medication is available for dispensing. For example, a physical button can be provided that the patient can activate. Further, a lever or switch can be provided that can be activated by the patient after receipt of the signal.

To monitor and verify that the dispensing of the drug is to the correct individual, an identification verification device, generally designated as 50, can be provided in outer housing 22 of dispenser 20 and can be connected to controller 30. Identification verification device 50 can be used to verify that the patient for whom the medication is to be given is present and ready for distribution of the medication. In this manner, identification verification device 50 can be used to verify the identity of the patient.

The identification verification device 50 can be a biometric identification device. For example, TRUEPRINT technology based fingerprint sensors offered by AuthenTec, Inc. of Melbourne, Fla., can be used as the fingerprint system 52. Fingerprint system 52 can comprise a touch screen 54 that can provide a place for the patient to place a finger. Fingerprint system 52 can then read the fingerprint and compare it to stored data to confirm that the individual trying to receive the medication is in fact the intended recipient.

Other identification verification devices such as retina scans, user passwords, voice recognition or the like can be used to verify the identity of the patient before distribution of the dose of medication within dispenser 20.

System 10 can further comprise a communication device 60 that can also be in operable communication with controller 30. Communication device 60 can be a wireless communication device. Such an electronic communication device 60 can operate on a wireless platform and can comprise an antenna 62 that transmits signals through a cellular network 64 to a remote facility, or location 70 that can house a database 72 for use in controlling dispenser 20. Database 72 can be accessed by the patient's doctor, pharmacy, and/or administrator of the medication system, as well as the patient. Through the wireless connection provided by cellular network 64, controller 30 can communicate through an Internet Service Provider 66 with the database 72 at the remote facility 70. Internet Service Provider 66 manages data collection and distribution to and from database 72 for the users. The users can comprise the patient, the patient's doctor and/or pharmacist, and/or the administrator of the medication system.

Through the Internet 68, appropriate individuals can gain access to the information provided to and from dispenser 20 to monitor and control the dosing of the medication. For example, such individuals or locations can comprise the patient, the doctor's office, the pharmacy, or the administration facility, where administrator resides. Authorized personnel from the doctor's office can gain access to patient and dispenser information stored on database 72 through a clinician browser 74. Authorized personnel from the pharmacy can gain access to patient prescription information stored on database 72 through a pharmacist browser 76. Authorized personnel from the administration facility can gain access to clinician, pharmacist, and dispenser information stored on database 72 through an administrator browser 78. Data stored can comprise information such as predetermined times to operate dispenser 20. The data can also comprise the name of the medication being distributed, the patient's data, the patient's compliance schedule, caregiver data, and compliance notification data as well as pharmacy data, physician data, insurance data, and emergency contact data. Further, such information can be provided on a data store connected to controller 30 within dispenser 20 itself.

Controller 30 can be programmable to connect to a predetermined Internet Service Provider 66 through electronic communication device 60 and cellular network 64 in order to transmit the patient's data and obtain a patient registration. Controller 30 can also be programmable to connect to Internet Service Provider 66 through electronic communication device 60 in order to transmit the compliance schedule and compliance notification data from database 72. Controller 30 can also be programmable to connect to Internet Service Provider 66 through communication device 60 in order to transmit or receive the pharmacy data, physician data, insurance data, and emergency contact data.

When controller 30 has received instruction that the signal has been received, controller 30 can transmit a compliance notification to Internet Service Provider 66 to be sent on to the physician, pharmacist, or administrator. Alternatively, the compliance notification can be sent to database 72 where the physician, pharmacist or administrator can access the notice of compliance. Similarly, if the recipient does not acknowledge the signal and the signal goes on for a predetermined time, controller 30 can send a signal to Internet Service Provider 66 to transmit a non-compliance notification that then can be forwarded on to the physician, pharmacist, or administrator as well as stored in the database as needed.

The user can use display screen 32 to communicate with controller 30 to order a refill of the medication or to order a new dispenser 20 containing the medication when the system is connected to the predetermined Internet Service Provider 66. In this manner, the user can take dispenser 20 back to the pharmacy to have it refilled or to pick up a new dispenser 20 which can be taken back and used by the patient. The interchangeable dispensers 20 provide a way to easily monitor the drugs that are placed into each dispenser 20 by the pharmacist. The pharmacist can ensure that the correct information is downloaded into controller 30 within the appropriate dispenser 20 for the appropriate patient before the patient picks that dispenser 20 up from the pharmacy or doctor's office.

Controller 30 can also be programmable to update and transmit the caregiver data and compliance notification data to the database or Internet Service Provider 66 and/or the clinician browser 74, pharmacist browser 76, or administrator browser 78 when the system is connected to Internet Service Provider 66. Controller 30 can automatically connect and send such information as needed or desired. Further, communication device 60 can receive notices from the predetermined Internet Service Provider 66 when the system is connected to the predetermined Internet Service Provider 66. Controller 30 can be programmable to receive and use notices as necessary to better manage dispenser 20. Similarly, controller 30 can be programmable to access and search databases provided by Internet Service Provider 66.

System 10 can also comprise a location determination device (not specifically shown) such as an integrated global positioning system ("GPS") receiver that can be contained within outer housing 22 of dispenser 20. For example, a location determination device can be integrated into controller 30. Such a device permits the location of dispenser 20 to be easily determined. If someone tries to steal dispenser 20 or dispenser 20 is misplaced, the patient can contact the administrator who can track down the location of dispenser 20. For example, the administrator can use tracking software and communication systems of a GPS system used within dispenser 20 for determining the location of that dispenser 20. In this manner, theft of the dispenser can be minimized, and, hopefully, the chances of the perpetrator being caught and prosecuted can be increased.

System 10 can also comprise a telephone modem within dispenser 20 that allows it to be hooked up to a telephone line to call for emergency assistance, if needed. Dispenser 20 can comprise an emergency assistance button 24 that can be actuated to cause controller 30 to dial an emergency telephone number. Dispenser 20 can also comprise a dispensing door 26 which can be used to permit access into dispenser 20 to remove a dose of medication. Dispenser 20 can also comprise a microphone 42 to allow for the patient to communicate with an emergency facility, which is contacted by controller 30.

Dispenser 20 can further comprise a lockout for disabling functionality of the system based upon predetermined criteria. Such a lockout can be in furtherance to identification verification device 50, which can also be used to prevent unwanted access to the medication contained in dispenser 20. However, the lockout can help to prevent overdosing of the patient or dosing of the patient when the patient is not in a condition to receive such medication. For example, the lockout can comprise a breath sensor 46 for determining a breath alcohol level. The breath alcohol level can then be compared to predetermined criteria that can comprise a maximum breath alcohol level that would be allowable for dispensing of the dose of medication from dispenser 20. The lockout can also comprise an interactive cognitive test on predetermined criteria that can comprise a minimum cognitive level based on the results of the test to allow dispensation of the dose of medication from dispenser 20. The interactive cognitive test can be performed through a display on the interactive display screen 32. In this manner, overdosing can be prevented as well as dosing of a patient who is too heavily medicated or disoriented to take the medication. Health hazards relating to the mixing of medications or alcohol with medications can be prevented. Based on the results from the lockout, an emergency contact, the doctor's office, pharmacy or a caregiver of the patient can be alerted that the patient is in a state that requires attention.

Figure 2:
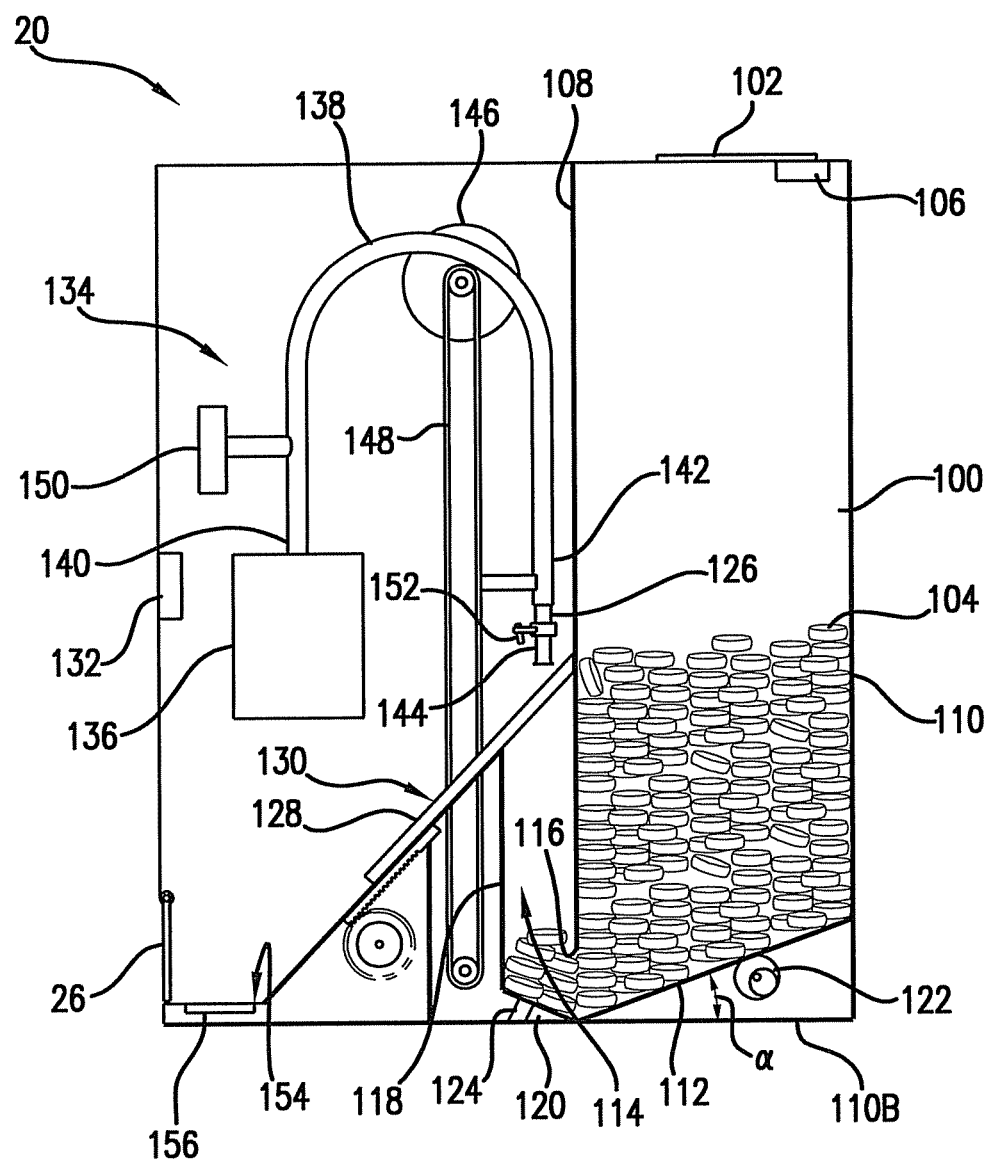
FIG. 2 illustrates a schematic of an embodiment of a dispenser device used within the system according to FIG. 1.

FIG. 2 illustrates a schematic internal view of dispenser 20. Dispenser 20 comprises a pill magazine 100 which can be filled at a pharmacy through a fill door 102. Fill door 102 can be locked to prevent access to the store of pills 104 within pill magazine 100. A tamper switch 106 can also be provided to monitor and record the opening of fill door 102 or other tampering that can occur to fill door 102 once dispenser 20 has left the pharmacy.

Pill magazine 100 can be defined by an inner wall 108 and an outer wall 110 and two side walls. Further, a slanting base surface wall 112 can extend within the dispenser 20 from the outer wall 110 downward to a bottom wall 110B forming an angle $\alpha$ with bottom wall 110B. Inner wall 108 can terminate short of base surface wall 112, thereby leaving an opening for pills to slide downward into a dispensing well 114.

Outer wall 110 and/or bottom wall 110B can be internal walls that can reside within outer housing 22 (shown in FIG. 1). Alternatively, outer wall 110 and/or bottom wall 110B can be external walls which help to form outer housing 22 of dispenser 20.

At a filling location such as a pharmacy, when fill door 102 is opened and pills 104 are placed into pill magazine 100, pills 104 flow downward under gravitational force to the base surface wall 112 and slide down its sloped surface which slopes downward from external wall 110 at angle $\alpha$. The pills 104 can slide into dispensing well 114 underneath end 116 of inner wall 108. A dispensing well wall 118 extends upward and parallel to inner wall 108 of pill magazine 100 to help define an opening in dispensing well 114. Dispensing well wall 118 permits only a small number of the pills from pill magazine 100 to fill the dispensing well 114 at any given time.

Dispensing well wall 118 can also comprise a slanted base wall 120 that slopes upward from the base surface wall 112 of pill magazine 100. A vibrator 122 can be used and positioned below base surface wall 112 to add vibration to base surface wall 112, thereby agitating pills residing on base surface wall 112. This vibration can cause pills 104 to fall or move down the sloped surface of the base surface wall into dispensing well 114. Vibrator 122 can be in communication with an optical detector 124 which can be placed along dispensing well wall 118 or base surface wall 120. Optical detector 124 can detect whether any pills reside in dispensing well 114. If optical sensor 124 does not detect the presence of pills 104 within dispensing well 114, then vibrator 122 can be activated to cause any pills residing in pill magazine 100 to slide down the slope surface of base surface wall 112. Optical detector 124 can be any conventional optical sensor known in the art.

Once it is determined that pills 104 reside in dispensing well 114, a vacuum pick up 126 can be actuated to pickup a pill 104 for delivery to dispensing door 26 of dispenser 20. The opening of dispensing well 114 can be opened and closed by motorized shutter 128, which can provide a slanted surface 130. When motorized shutter 128 is in a closed position as shown in FIG. 2, pills 104 within pill magazine 100 and dispensing well 114 are prevented from removal from dispenser 20.

A tilt sensor 132 can be provided which can be activated when dispenser 20 is tilted to prevent its operation while inverted or shaken. Tilt sensor 132 can be in communication with controller 30 (see FIG. 1). Such information as whether dispenser 20 is shaken or tilted can be sent from tilt sensor 132 to controller 30. Controller 30 can then render dispenser 20 inoperable and it can also forward a message to Internet Service Provider 66 and onto the clinician browser 74, pharmacist browser 76, or administrator browser 78 (see FIG. 1). Tilt sensor 132 can be a conventional equilibrium sensor. Tilt sensor 132 can also be configured to shut down dispensing operations directly if tilting or shaking is detected.

Dispenser 20 also can comprise, as noted above, a vacuum pickup 126, which can be a part of a vacuum mechanism 134 for removal of at least one pill from dispensing well 114 for delivery to dispensing door 26 of dispenser 20. Vacuum mechanism 134 can comprise a vacuum pump 136 that creates a negative pressure that can be used to pick up a pill 104 from dispensing well 114. Vacuum mechanism 134 can also comprise a vacuum tube 138 that is connected to vacuum pump 136 on one end 140 such that the negative pressure created within vacuum pump 136 creates a vacuum through vacuum tube 138. Vacuum pickup 126 can be secured on the other end 142 of vacuum tube 138. Vacuum pickup 126 as well as vacuum tube 138 can be extended into dispensing well 114 to retrieve a pill therefrom.

Vacuum pickup 126 can comprise a vacuum cup 144 disposed at its end distal from vacuum tube 138. Vacuum pickup 126 can be raised and lowered by a step motor 146. In the embodiment shown, step motor 146 can rotate a belt 148 which is secured to the vacuum pickup 126. By running step motor 146 in one direction, vacuum pickup 126 is lowered. By running step motor 146 in a reverse direction, the rotation of belt 148 can be reversed and vacuum pickup 126 can be raised.

A vacuum sensor 150 can be in communication with vacuum mechanism 134. Vacuum sensor 150 can detect whether or not a pill is stuck to the vacuum pickup 126 at vacuum cup 144 thereof. In this manner, vacuum mechanism 134 determines when a pill is secured to vacuum pickup 126 so that it can be raised from dispensing well 114 and ready for delivery to dispensing door 26 of dispenser 20.

In operation, once the patient has acknowledged receipt of the signal indicating time for the receipt of a dose of medication and the patient has identified himself or herself to system 10, dispenser 20 is ready to dispense a dose of medication to the intended recipient. When a pill 104 is to be dispensed, motorized shutter 128 can be moved from its closed position as shown in FIG. 2 to an open position (see FIGS. 3A and 3B) to allow vacuum pickup 126 to be lowered into dispensing well 114. As noted above, tilt sensor 132 can prevent shutter 128 from opening if dispenser 20 is tilted, inverted or shaken.

Optical sensor 124 can check to determine if any pills 104 are in position within dispensing well 114 to be picked up by vacuum pickup 126. If no pills 104 have fallen into dispensing well 114, vibrator 122 vibrates base surface wall 112 to agitate base surface wall 112 within pill magazine 100 to cause any pills 104 within pill magazine 100 to fall down the sloped surface of base surface wall 112 into position within dispensing well 114. As noted above, base surface wall 112 can be at an angle α as measured from the bottom outer wall 110B that provides enough of a slope to encourage pills 104 to slide into dispensing well 114.

As vacuum pickup 126 is lowered, vacuum pump 136 creates negative pressure which creates a vacuum suction through vacuum cup 144 of the vacuum pickup 126. As vacuum cup 144 comes in contact with a pill and thereby seizes the pill through vacuum pressure, vacuum sensor 150 detects that a pill is stuck to vacuum pickup 126. Step motor 146 can then be run in reverse, such that vacuum pickup 126 is raised out of dispensing well 114.

Optionally, an optical detector 152 can be secured to vacuum pickup 126 to make sure a pill is in position for pickup. Optical detector 152 optically determines if a pill resides within dispensing well 114 that can be picked up through vacuum pickup 126. If no pill is sensed by the optical detector 152, then vibrator 122 can be run. Vacuum pickup 126 can be lowered by step motor 146 by rotating belt 148 in a specified direction until optical detector 152 detects a pill at the pickup. Vacuum pump 136 starts creating a negative pressure that lifts the pill to vacuum cup 144. Vacuum sensor 150 then detects that a pill is stuck to vacuum pickup 126. If a pill is detected, vacuum pickup 126 is raised by reversing step motor 146 so that belt 148 raises vacuum pickup 126.

Once vacuum pickup 126 with the pill attached to vacuum cup 144 has cleared dispensing well 114, motorized shutter 128 can then be moved into a closed position of the opening in dispensing well 104 as shown in FIG. 2. At this point, the vacuum pump 136 can shut off, allowing the pill to fall against slanted surface 130 of shutter 128. The pill can fall to a removal position 154 at dispensing door 26 of dispenser 20. An optical sensor 156 can be placed in proximity to removal position 154 to detect that the pill is in place before allowing access to the pill through dispensing door 26. If no pill is detected, then the steps of picking up a pill through vacuum pickup 126 can be repeated until it is recognized that a pill is in position for removal from dispensing door 26 of dispenser 20. Vacuum pickup 126 can be recessed slightly into the body of dispenser 20 to ensure that the pill attached thereto drops freely when the vacuum is removed.

Figure 3A:
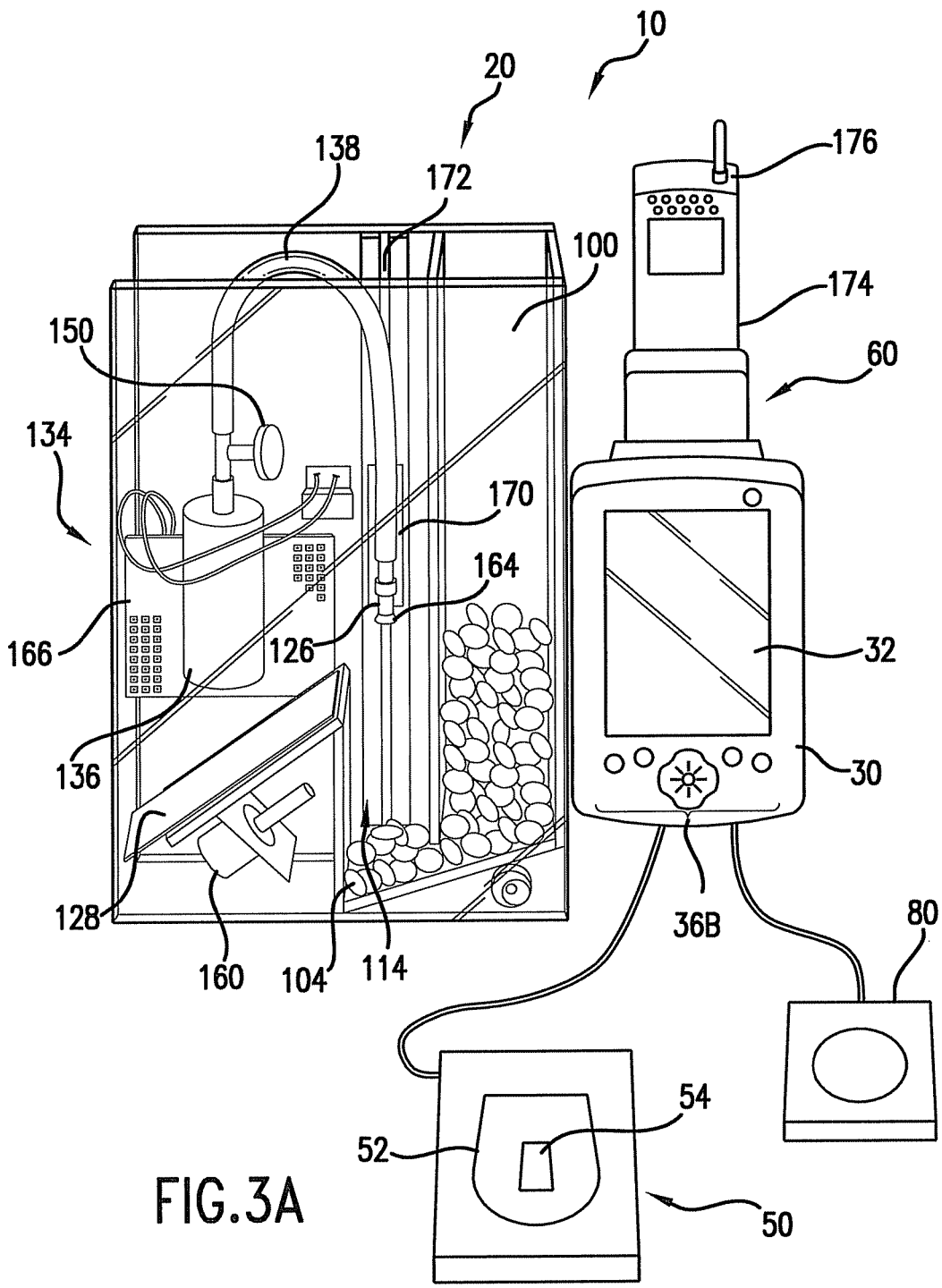
FIGS. 3A-3C illustrate perspective views of components of an embodiment of a system for a point-of-use medication control according to the present subject matter.
Figure 3B:
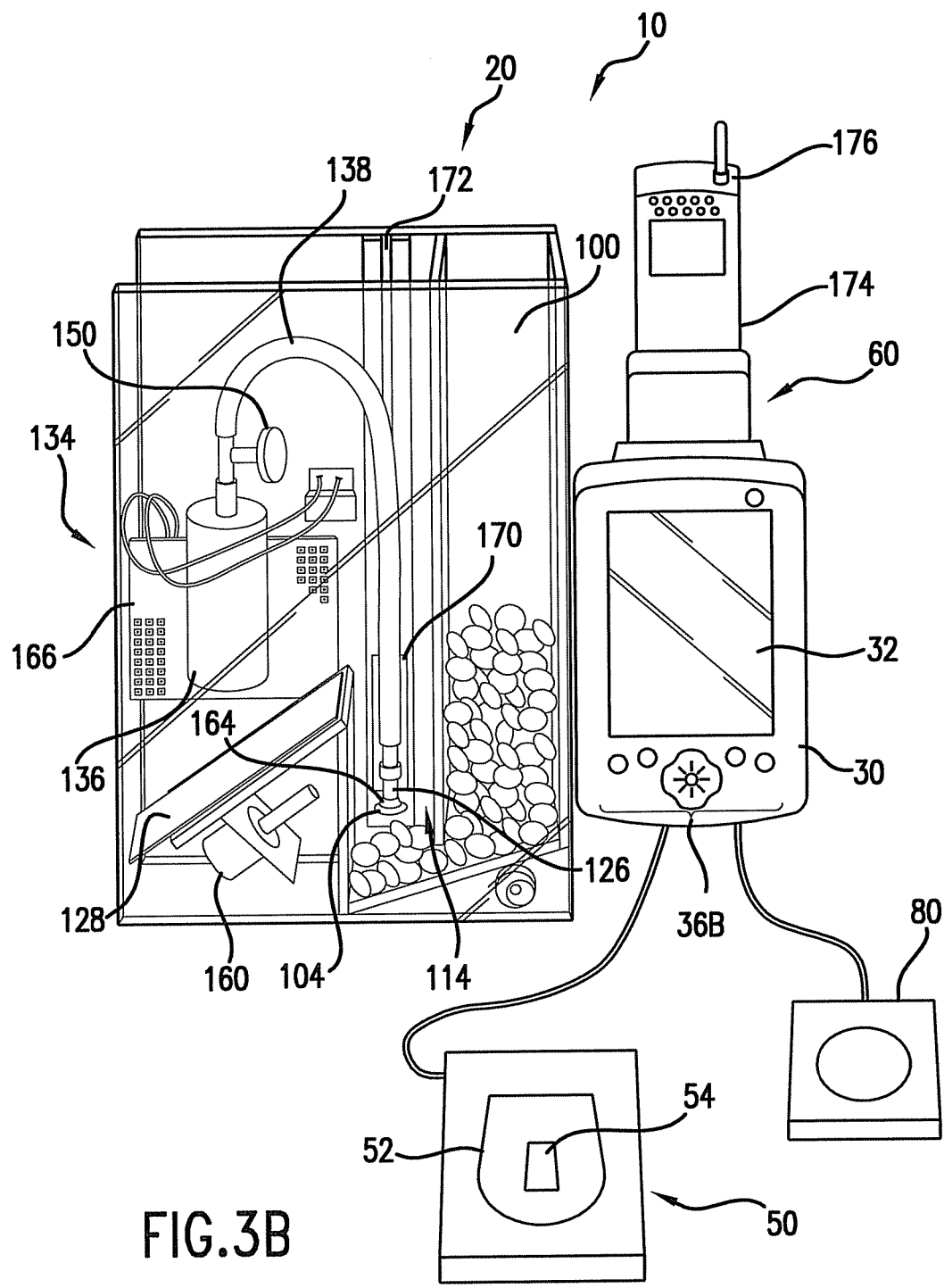
Figure 3C:
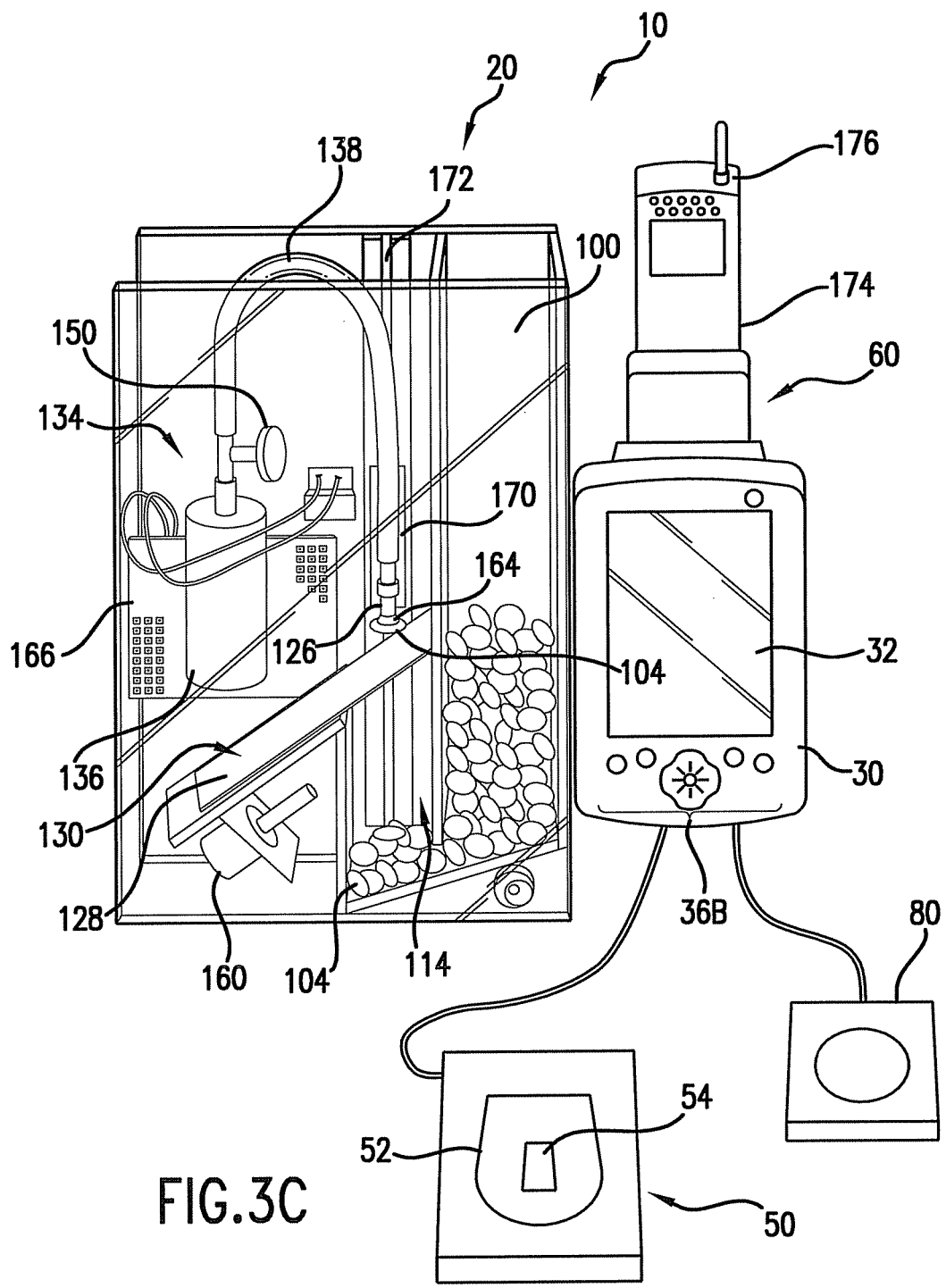

FIGS. 3A, 3B, and 3C illustrate components of an embodiment of a system 10, including a dispenser 20 outside of its outer housing that can be used to enclose dispenser 20 and the other components. The components are shown free standing relative to one another and can be arranged in any known manner that provides necessary access to any interactive component that the patient must engage to receive the intended doses of medication. Dispenser 20 can comprise pill magazine 100, vacuum mechanism 134, and motorized shutter 128 as well as dispensing well 114. A controller 30 as well as an identification verification device 50 can also be included as components of system 10. Further, a location determination device 80 can be included in system 10. As noted above, location determination device 80 can be a GPS device that can easily be used to locate the whereabouts of the system 10.

Controller 30 can be a microcomputer such as a personalized digital assistant ("PDA"), for example, an Ipaq 3635. Controller 30 can also be a computer, programmable logic controller, or the like. Controller 30 can operate using any compatible operating system. For example, controller 30 can operate using Microsoft Pocket PC. Controller 30 can provide a display screen 32 which can be a touch-tone interactive display. Further, controller 30 can provide physical buttons 36B which control a cursor on display screen 32 to allow interaction between the patient-user and the controller 30.

Controller 30 can be in communication with identification verification device 50 in the embodiment shown. Identification verification device 50 can be a fingerprint reader 52 which has a touch screen 54 on which a patient-user can place a finger in order for the fingerprint reader 52 to read the user's fingerprint.

Controller 30 can also be in communication with vacuum pump 136 of vacuum mechanism 134 as well as a step motor 160 that is used to control shutter 128 for opening and closing of shutter 128 to provide access through the opening in dispensing well 114. Further, controller 30 can be in communication with step motor 162 (shown in FIG. 4) used to raise and lower vacuum pick up 126 through a slide 170 to which vacuum cup 164 is attached. Slide 170 rides within a slot 172 that extends downward into dispensing well 114. Vacuum sensor 150, which is used to determine the presence of a pill on vacuum pump 164, also can be in communication with controller 30.

Vacuum mechanism 134 components can be controlled by a separate vacuum controller 166 as shown in FIGS. 3A-3C and 4 that is in communication with the controller 30. Such vacuum controller 166 can be a Parallax microcontroller offered by Parallax, Inc., of Rocklin, Calif. Controller 30 can direct operation of vacuum mechanism 134 by communicating with vacuum controller 166. In other embodiments, controller 30 can directly control vacuum mechanism 134 and its components.

Location determination device 80 can be in communication with controller 30 to pass location information to the controller 30 and onto a remote facility 70 or Internet Service Provider 66 (See FIG. 1). Further, location determination device 80 can produce a signal that is independent of controller 30 and communication device 60 that is detectable by an appropriate positioning system such as a GPS. In such embodiments, the signal from the location determination device 80 can be picked up by the administrator as needed.

All components of system 10 can share a common battery power supply (not shown). All components of system 10 can also communicate with controller 30 via an RS232 serial interface.

In operation, controller 30 can be preloaded and programmed with dispensing instructions as to the times of use at the location where dispenser 20 is filled. Programming and fingerprint template transmission also can be done remotely. A patient's fingerprint would only need to be enrolled once for use on multiple units.

Pill magazine 100 of dispenser 20 can store a single type of pill or capsule therein. Pill magazine 100 can be filled at a pharmacy. Dispenser 20 can then be secured to prevent access to pill magazine 100 or prevent unauthorized removal of the pill or capsule from dispenser 20. As described, a fill door (not shown) can be used to fill pill magazine 100. The fill door can then be locked and a tamper switch can be used to detect any opening of the fill door.

Once controller 30 determines it is time to dispense medication to the patient, a signal can be sent out to notify the patient that it is time to receive a dose of medication. For example, a visual signal can be shown on display screen 32 to notify the patient of availability of the dose of medication. Additionally, or alternatively, an audible signal through a speaker system (not shown) can be sent out by controller 30 to alert the patient of the availability of a dose of medication. The patient can acknowledge receipt of the signal through use of buttons 36B. Then, the patient can verify his or her identity through identification verification device 50. The patient can interact with system 10 via display screen 32 of controller 30, or through buttons 36B of controller 30, to verify the cognitive level of the patient through cognitive tests. Additionally, or alternatively, a breath analyzer mechanism can be provided to discern the alcohol level within the bloodstream of the patient to ensure no ill effects of mixing the medication and alcohol will result from allowing dosage to be dispensed to the patient. Once identification has been verified and any cognitive tests which can be employed have been fulfilled, controller 30 can instruct vacuum mechanism 134 to remove a pill or capsule for distribution to the patient.

At such time, step motor 160 can drawn back shutter 128 such that dispensing well 114 is opened to allow vacuum pick up 126 to enter dispensing well 114 to remove a pill or capsule disposed therein as shown in FIG. 3A. As discussed above, a tilt sensor can be disposed within the dispenser that identifies when the machine is titled, inverted, or shaken. In such instances, shutter 128 is placed immediately into a closed position, if it is not already in that position, and dispenser 20 is rendered inoperable. Further, dispenser door 26 can be secured in a shut position to prevent removal of any pills, and controller 30 can send a signal to the appropriate locations to notify doctors, pharmacist, or an administrator of the unauthorized use of dispenser 20.

Figure 4:
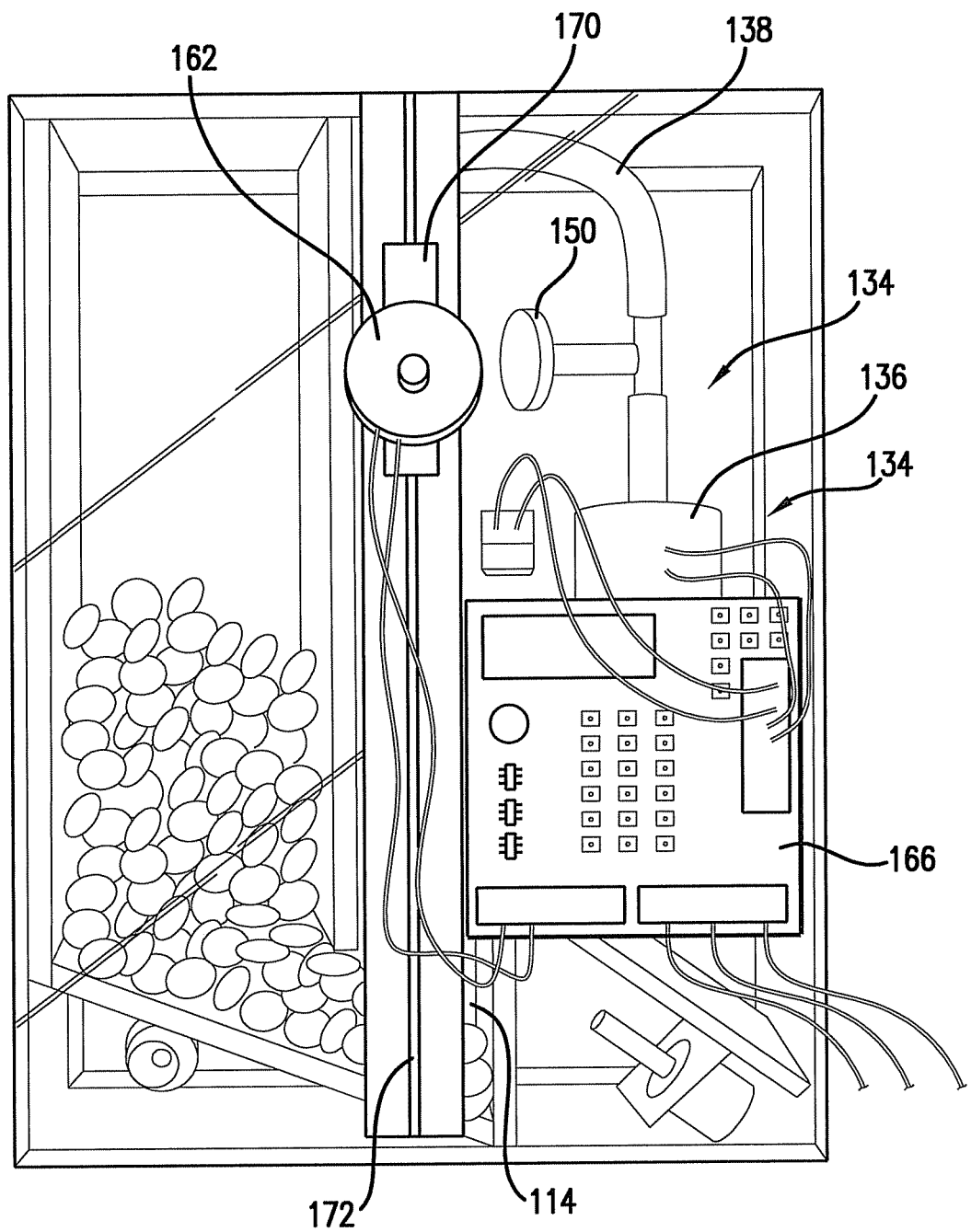
FIG. 4 illustrates a backside perspective view of a component of the embodiment of the system for a point-of-use medication control according to FIGS. 3A-3C.

Once shutter 128 is in an open position as shown in FIG. 3A, vacuum pick up 126 with its vacuum cup 164 can be inserted into the well through the motion of step motor 162. In the embodiment shown in FIG. 4, step motor 162 operates a slide 170 in a conventional manner, so that slide 170 is moveable along a slot 172. For example, slide 170 may be attached to a belt (not shown) that can be rotated in a forward or reverse direction by step motor 162. Slot 172 can run parallel to dispensing well 114 and can extend above dispensing well 114 as shown in FIG. 4. Vacuum pickup 126 (shown in FIGS. 3A-3C) can be secured to slide 170 such that vacuum cup 164 extends downward. Vacuum cup 164 can be a bellow type vacuum cup, which easily secures to a pill or capsule once placed under a negative pressure.

Once shutter 128 is moved to its open position through step motor 160, vacuum pickup is lowered by step motor 162 into dispensing well 114. Controller 30, or alternatively the vacuum controller 166 as shown in FIG. 4, can start vacuum pump 136 to create a negative pressure through vacuum tube 138. This negative pressure creates a vacuum through vacuum cup 164 at the end of vacuum pickup 126. As shown in FIG. 3B, step motor 162 lowers vacuum pickup 126 into dispensing well 114 such that vacuum cup 164 comes in contact with a pill or capsule. The negative pressure created by vacuum pump 136 pulls the pill or capsule against vacuum cup 164 such that the pill or capsule is held by vacuum cup 164 for removal from dispensing well 114. Controller 30, or vacuum controller 166, verify by vacuum sensor 150 that vacuum cup 164 has picked up a pill or capsule. At this point, controller 30, or vacuum controller 166, will then instruct step motor 162 to raise vacuum pickup 126 out of dispensing well 114. Vacuum sensor 150 will continue to monitor to ensure that a pill or capsule is secured by vacuum cup 164. Once the step motor 162 has raised vacuum pickup 126 to a predetermined point above dispensing well 114, controller 30, or vacuum controller 166, will instruct step motor 162 to close shutter 128 as shown in FIG. 3C.

Once vacuum pickup 126 with a pill or capsule attached to vacuum cup 164 is raised above dispensing well 114, shutter 128 can be closed. Controller 30, or vacuum controller 166, can turn off vacuum pump 136. Thereby, the negative pressure is removed from the vacuum pickup 126 and vacuum cup 164 allows the pill or capsule secured thereto to drop onto slanted surface 130 of shutter 128. Slanted surface 130 feeds the pill or capsule into the chute and down to removal position 154 in front of dispenser door 26 as shown in FIG. 2. At this point, the pill or capsule is ready for removal from dispenser 20 by the patient or caregiver.

Once the patient has used a fingerprint touch sensor 52 to confirm identity and the proper number of pills or capsules are dispensed and removed, controller 30 can record the removal of the pills. After dispensing medication on timed intervals, controller 30 can activate a cellular modem 174 of a communication device 60 and connect to a computer server to exchange data with the Internet Service Provider server and the database that contains tables for patients, pharmacists and dispensing units. For example, information can be exchanged twice a day. Further, information can be provided to the patient's doctor, pharmacist and the administrator of the outpatient medication system. In this manner, data can be exchanged between controller 30 and the computer which provides access to other necessary parties including the patient through the cellular modem 174 and antennae 176 of the electronic communication device 60, both of which are in communication with controller 30. For example, dose history can be sent to the server in this manner. Further, if the dispenser is reported as lost, the server can communicate with the dispenser, while the location determination device 80 can be used to identify the location of the dispenser. Once the location is determined, coordinates are then relayed to the server so the dispenser can be located and recovered.

Software running on the database server 72 (see FIG. 1) can comprise an SQL database to store information about dispensation, enrolled patients, prescription, and doctors (clinicians). This data can be served out to dispensers as described above and also to authorize users via Internet 68 using a web browser based interface as discussed below.

Figure 5A:
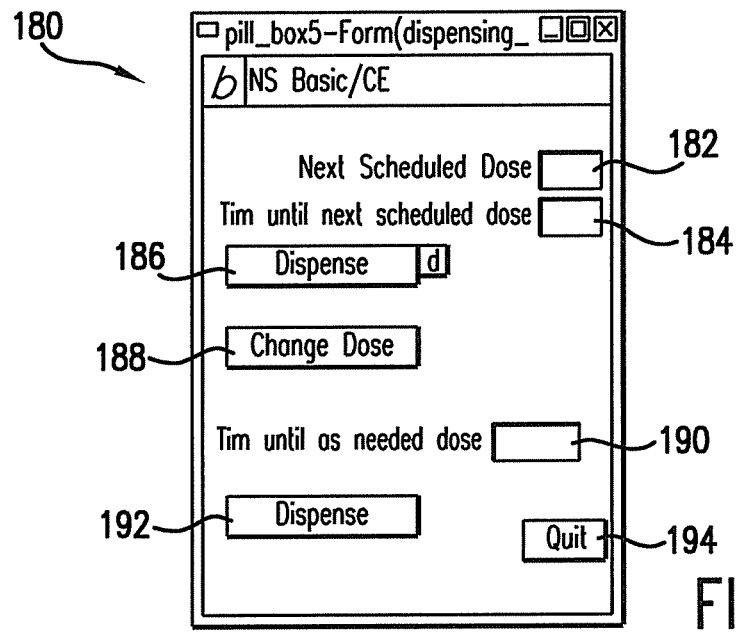
FIGS. 5A-5E illustrate interactive screen display windows used for user interaction with a controller of an embodiment of a system for a point-of-use medication control according to the present subject matter.
Figure 5B:
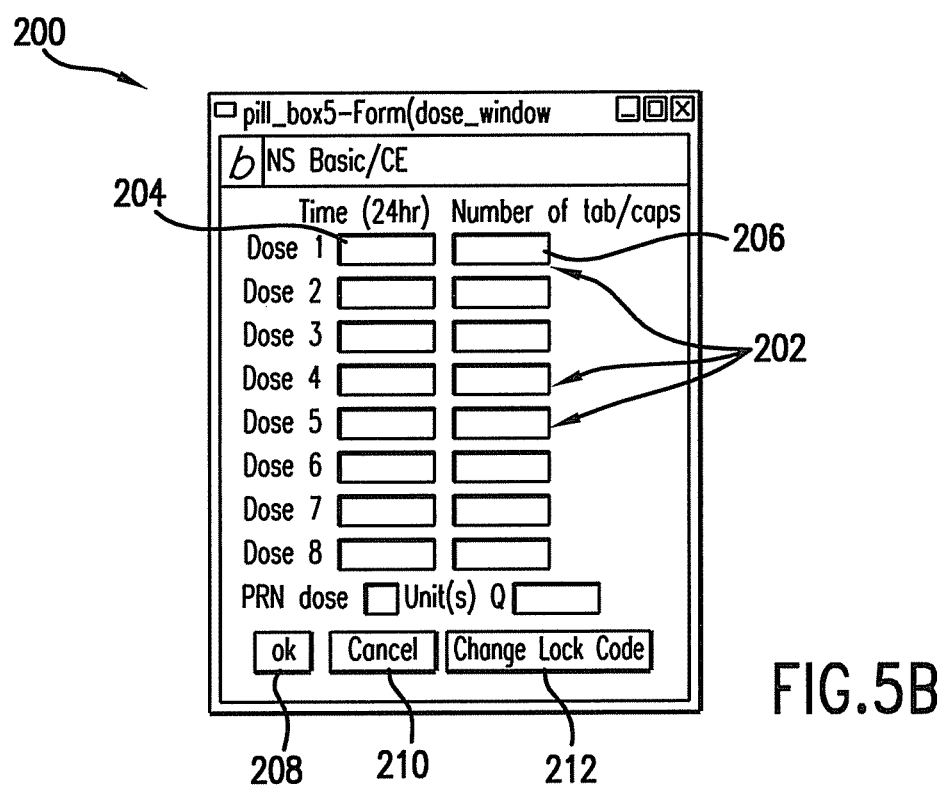

For embodiments which use a graphical user interface that is displayed on the display screen 32 of the controller 30, the user interface requires very little input from the patient. As shown in FIG. 5A, a dispensing window 180 shows a cell 182 for the next medication dose and a countdown timer cell 184 for that dose. The top dispense button 186 provides a button to dispense the regularly scheduled medication dose. However, the regularly schedule dose can be dispensed through other mechanisms such as by verifying the identity of the patient through an identification verification device. The change dose button 188 is not for use by the patient but is used by the doctor, pharmacist and/or the administrator of the out-patient medication system. Such a change dose button 188 is code locked.

Extra doses which can be provided for certain ailments such as migraines, anxiety, and pain medications, can be handled by the bottom half of the window 180. A countdown timer cell 190 shows when an extra dose is or will be available. The second dispenser button 192 activates the dosing cycle. The quit button 194 can be provided to end the dispensing program.

A dosing window 200 illustrated in FIG. 5 can be provided for pharmacy access to medication directions. The window 200 can be code locked to prevent access by unauthorized users. The window 200 can be accessed through the dispensing window 180 after the correct access code has been entered. Ideally, only the pharmacy has the correct code to unlock and gain access to the dosing window 200 as shown in FIG. 5B. The dosing window 200 comprises dosing cells 202 that provide the time identifier 204 for each dose as well as amount identifier 206 for each dose. In this manner, scheduling time for each dose can be set by the pharmacist before dispenser 20 leaves the pharmacy. Approval button 208 is provided to approve the dosing schedule provided in dosing cells 202 once a scheduled time and dosage has been entered. A cancel button 210 permits canceling of the dosing schedule provided in dosing cells 202. In the embodiment shown, eight dosing cells 202 are provided, but not all of these cells 202 need to be used. For example, only four doses can be necessary within a 24 hour period. Thus, only four sets of dosing cells will need to be used. Further, if necessary, more dosing cells 202 can be provided.

A change lock code button 212 can be provided to change the lock code needed to gain access to the dosing window by the pharmacist. Dosing window 200 does not have to be used by the pharmacist. The controller of the system can be easily programmed via internet access to the central database which then can be communicated to the controller contained within the dispenser in the care of the patient. In the event that the internet access is unavailable, dosing window 200 allows programming access to authorized individuals.

Figure 5C:
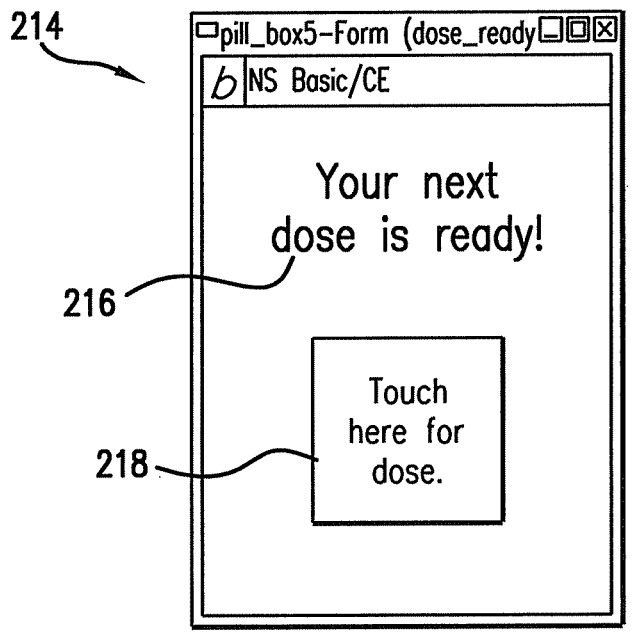

FIG. 5C illustrates dosing ready window 214 that alerts the patient that the medication is ready to be taken. As noted above in regards to the dose ready window shown on screen 32 of FIG. 1, the alert can comprise the activation of a signal light, tone, vibration, or voice prompt, thereby providing both visual and audio signals to alert the patient that a dose is ready. The dose ready window 214 can comprise a message 216 which alerts the patient to the fact that a dose is ready. Further, the dose ready window 214 can comprise an acknowledgement button 218 that can be activated to acknowledge receipt of the signal and thereby prompt the user to engage the finger sensor for activation of the dispenser to provide a dose of the medication.

Figure 5D:
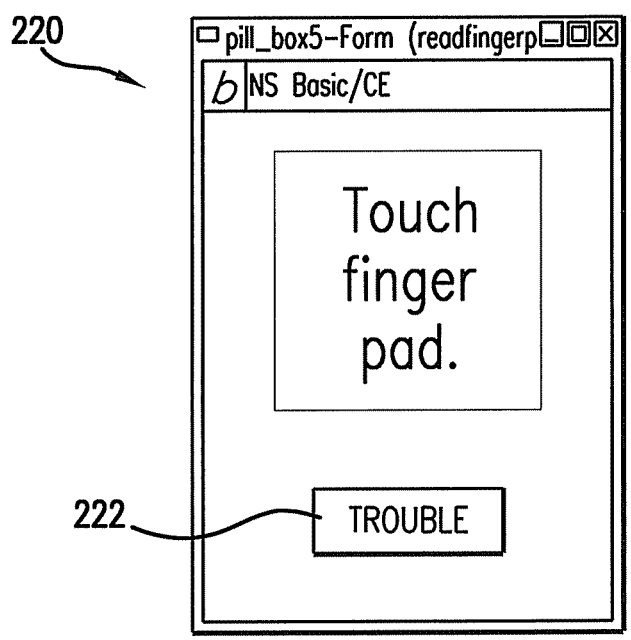

Once the signal screen shown in FIG. 5C is acknowledged through touching of the acknowledgement button 218, a fingerprint reading window 220 as shown in FIG. 5D can be displayed on display 32 to prompt the patient to touch a fingerprint sensor for positive identification of the patient before dispensing of the dose of medication. The fingerprint sensor provides rapid, reliable, and easy use and demands very little of the patient. Use of this identification verification device verifies that the patient is present at the time the medication is made available. The sensors on the system further check to see that the dose is picked up. While the system does not guarantee that the medication goes from hand to mouth of the patient, it can eliminate every barrier except willful refusal. If the patient is having trouble then a trouble button 222 can be provided that serves to trigger a transmission to a central database that technical support is needed. If finger reading proves to be a persistent problem, the use of the fingerprint reader can be bypassed.

Figure 5E:
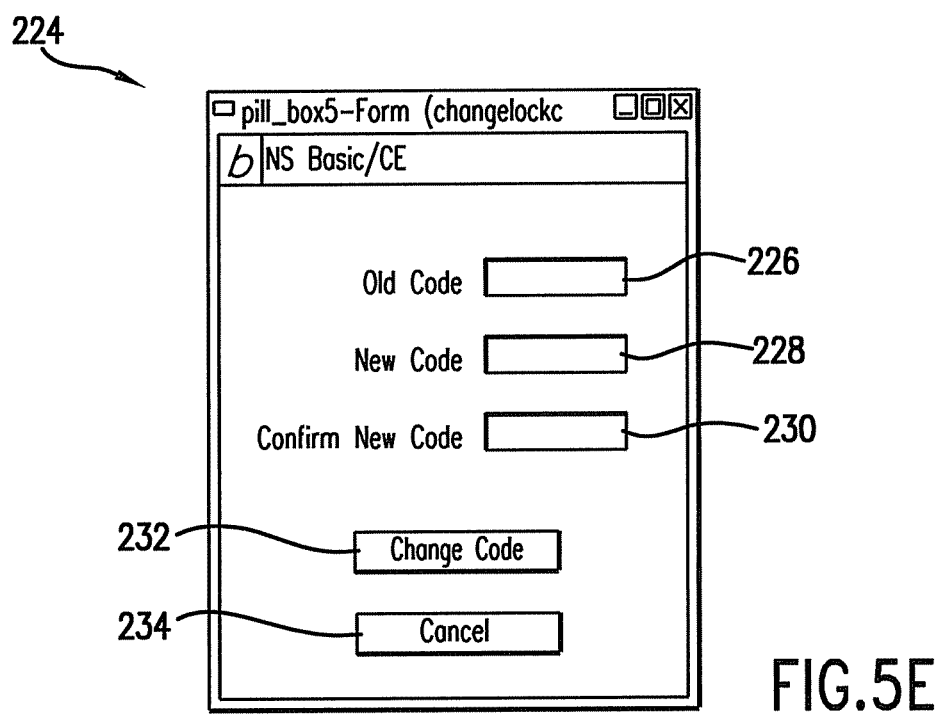

Further, the display window can provide a graphical user interface for changing the lock code as shown in FIG. 5E. A change lock code window 224 provides the ability of the pharmacist to change the lock code to prevent unauthorized access to the dosing window which can be used to alter the dosing schedule and amounts of the dosing of the medication. Change lock code window 224 can comprise cells to enter the old code at cell 226, enter a new code at the new code cell 228 and confirm the new code at confirmation cell 230. Once the new code is typed into both the new code cell 228 and the confirmation cell 230, a change code button 232 can be activated to change the lock code. Thereby, the old code can be changed to a new code that controls the access to the dosing window 200. If the code typed into the new code cell 228 and confirmation code 230 do not match, the new code must be re-entered in both cells 228, 230. If the pharmacist does not wish to change the code, a cancel button 234 is provided to close the change code lock window 224.

A server can be used to store a database program that can comprise the central database 72 as shown in FIG. 1. For example, an Apple G5 server available from Apple Computer, Inc., of Cupertino, Calif., can run OpenBase 9.0, an SQL database program, available from OpenBase International, Ltd., of Concord, N.H., that can comprise the central database. An example of a structure of database 72 is shown in FIGS. 6-13. In particular, an array table database structure is described, although it is to be understood that other common forms of databases can be used. Further, different data can be collected, stored and used within database 72 other than the specific examples shown in FIGS. 6-13. FIGS. 6-13 are screen shots of a user interface for the database. Database 72 holds and distributes information on the doctors, patients, prescriptions, pharmacist, and dispenser units. Within the screen shots of FIGS. 6-13, different verbiage and words can be used to describe the same item. For example, dispensers can be called "trackers" within the screen shots of the particular embodiment of the database. Also, doctors and/or pharmacist can be identified by the term "Clinicians." The data interconnections can be shown within the Figures. The data fields of each table are also listed. Fields can be added or removed as needed. These changes are dynamically added to the web interface.

Figure 6:
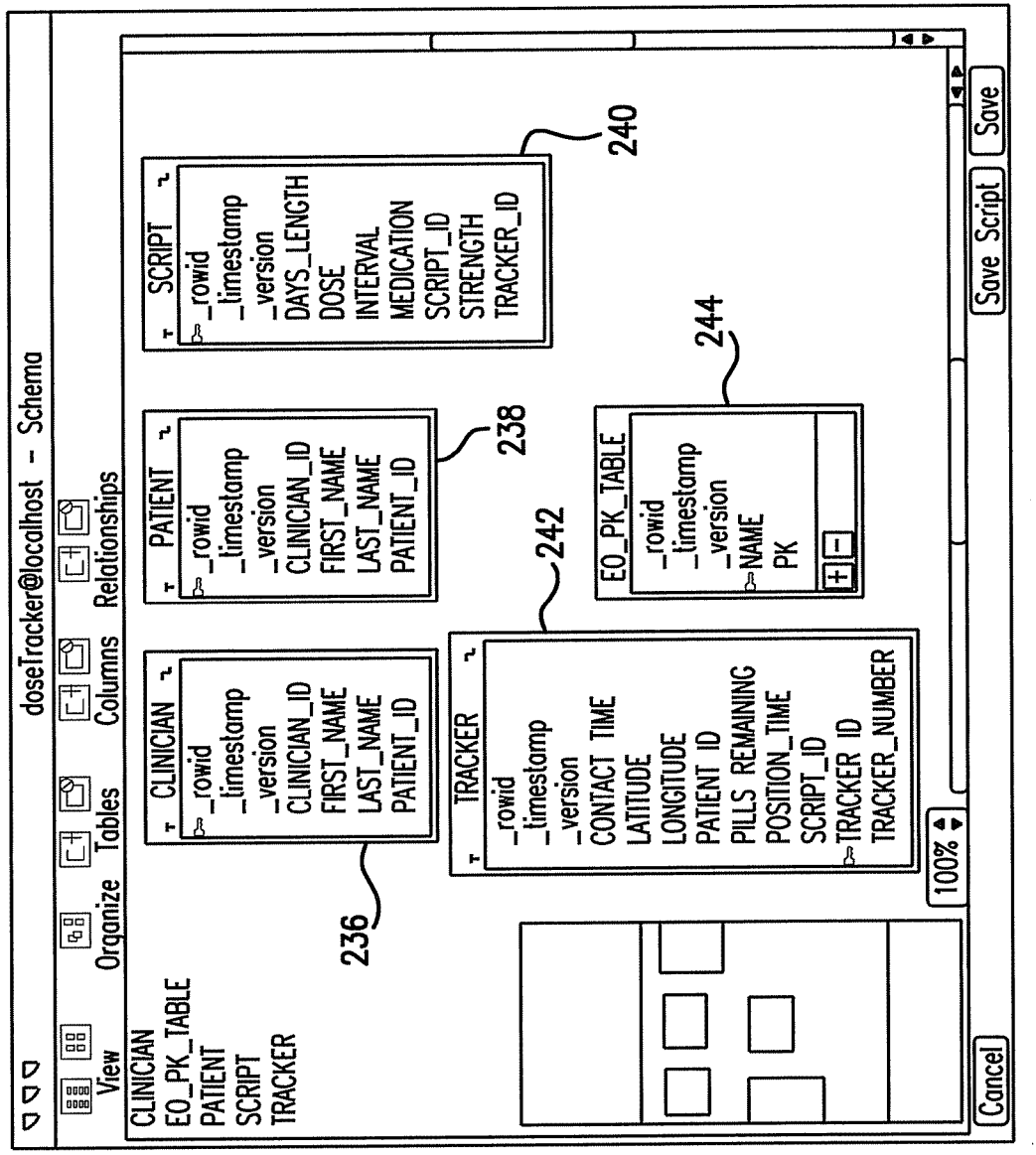
FIG. 6 illustrates a schematic representation of embodiments of possible data tables used within a database of an embodiment of a system for a point-of-use medication control according to the present subject matter.

As shown in FIG. 6, an array table can be provided for the clinician, patient, script, tracker, and EO_PK_table. These array tables contain different interconnected information. A clinician table 236 can comprise fields for the row ID, time stamp, version, clinician ID, the first name and last name of the clinician and patient ID. Similarly, a patient table 238 can have the fields for the row ID, time stamp, version, clinician ID, the first name and last name of the patient and patient ID. A script table 240 can comprise fields for row ID, time stamp, version, length of time in days, dose amount, the interval between doses, the medication, the script ID, the strength level of the medication, and tracker ID for each dispenser. Script table 240 can comprise information that would appear on a prescription or prescription bottle. A tracker table 242 corresponds to the information about the dispenser used by the patient. The fields of the tracker table 242 comprise row ID, time stamp, version, contact time, patient ID, pills remaining, script ID, tracker ID for each dispenser, and tracker number for each dispenser. Also, the fields within the tracker table can also comprise longitude and latitude of the dispenser provided by a location determination device, such as a GPS device, within the dispenser as well as the position time also provided by the location determination device within the dispenser.

The EO_PK_table 244 comprises a row ID, time stamp, version, name, and primary key information. The EO_PK_Table is a database programming table used in setting up enterprise objects and primary keys within the database. The EO_PK_Table can be used to verify access to different data and is used to assign primary key attributes to the data entered and aids in placement within the right tables. The EO_PK_Table is automatically generated by the database software. The EO_PK_Table may not be necessary depending on the database software and structure used.

Figure 7:
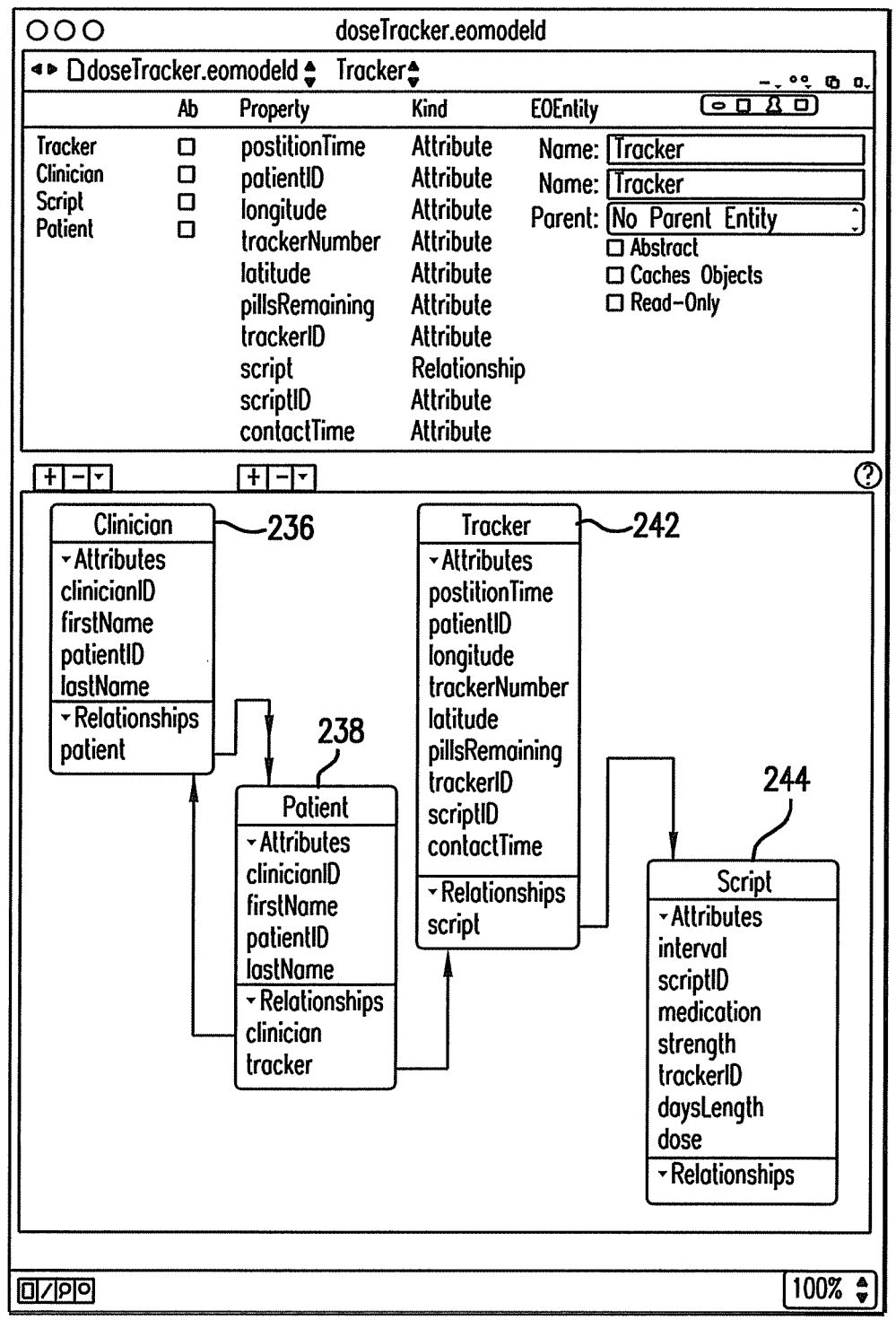
FIG. 7 illustrates a schematic representation of interactions between the data tables of FIG. 6.
Figure 8:
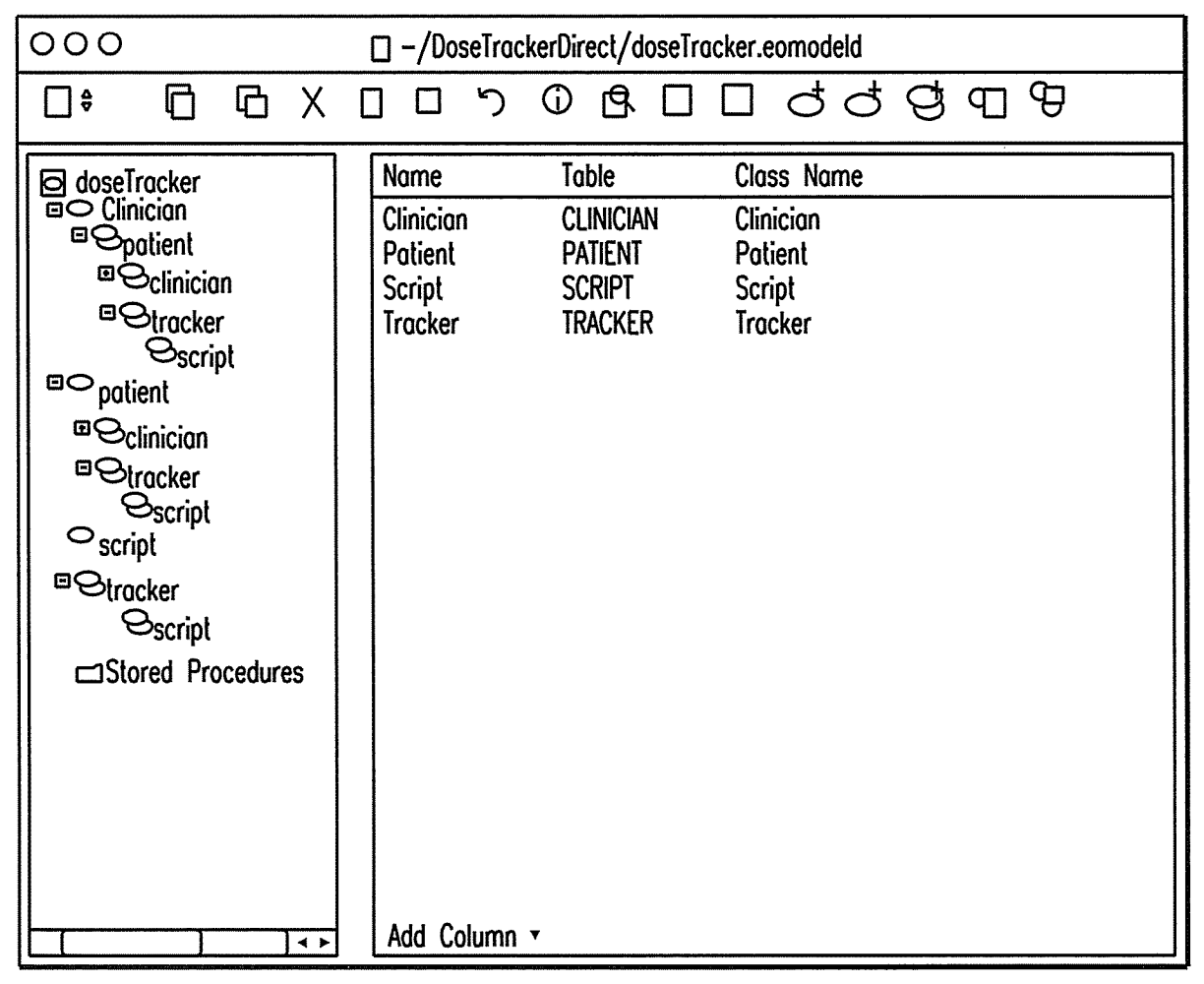
Figure 9:
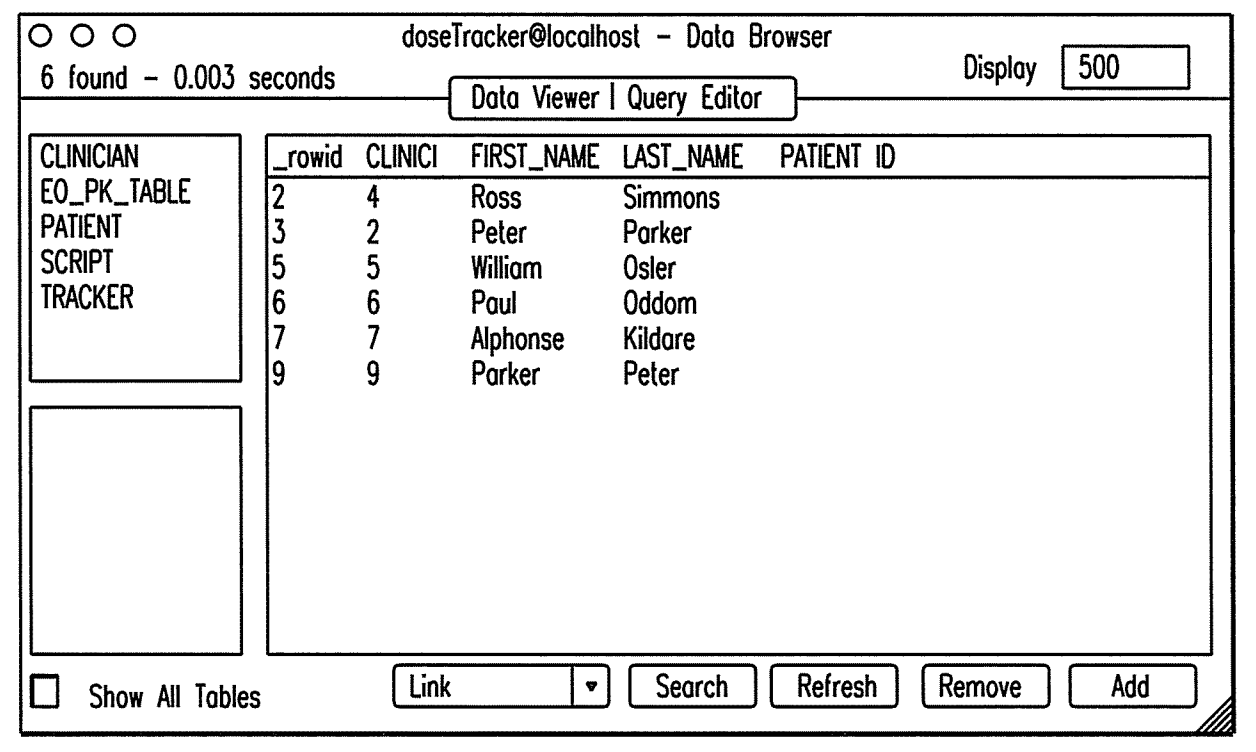
Figure 10:
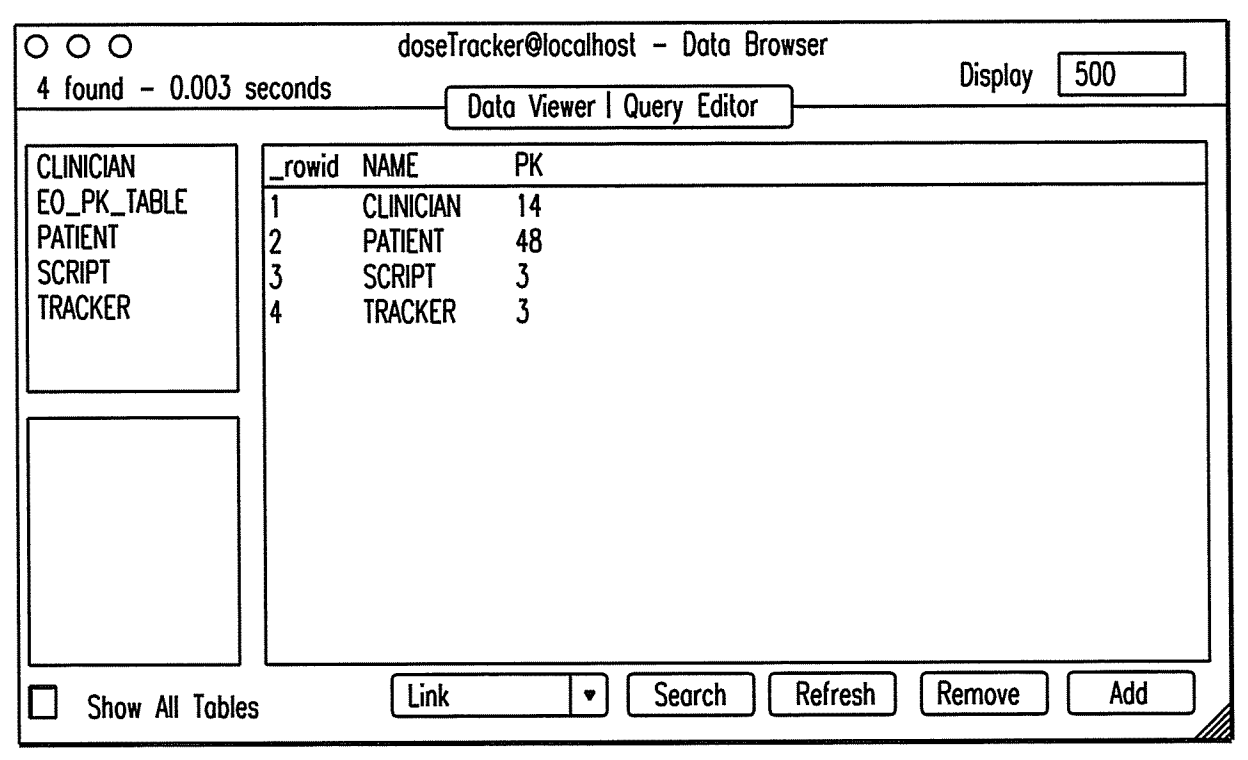

FIG. 7 shows the shared data fields and relationships between the different tables. For example, information is shared between clinician table 236 and patient table 238. Patient table 238 also shares information with tracker table 240 which in turn shares information with script table 242. In this manner, when certain information is updated within one of the tables, this information can be passed on to other associated tables. FIG. 8 shows a screen shot of an upper level screen which identifies the different tables by class names and names. FIGS. 9 and 10 show screen shots of data view information. In particular, FIG. 9 illustrates a clinician table identifying the clinician by the clinician's ID and his or her first and last name. FIG. 10 illustrates the top most level of the database.

FIG. 11 shows a patient table which identifies the patient by his or her first and last name in the fourth column and patient ID in the fifth column. The patient table provides a column for clinician ID to identify the clinician for each patient. Each row contains specific information for the patient within that row and assigns each patient a patient ID number displayed in column 6.

Figure 12:
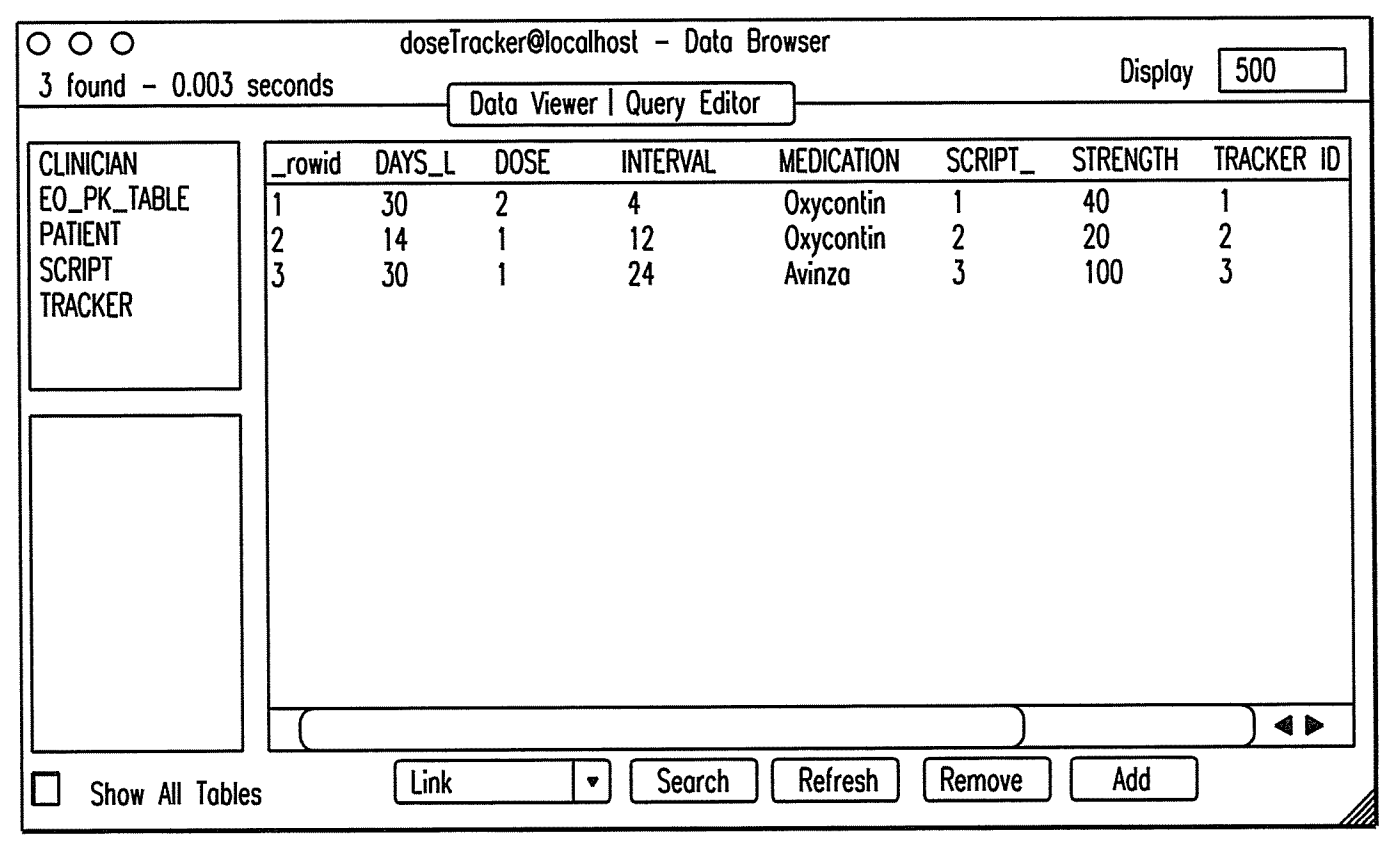

FIG. 12 shows a script table which identifies the number of days for which the medicine in each row is to be taken and the amount of the dose to be given as well as the interval measured in hours between doses. The script table also provides the name of the medication being administered and the strength of the medication. The script ID is provided as well as the tracker ID which is used to administer and dispense the associated medication at the appropriate doses and intervals. The script table can also comprise information on each dose scheduled to be taken within a 24 hour period instead of relying just on the interval information. This would allow for greater dosing flexibility. Information regarding the amount of time that a dose will be available after it is due can be provided in the script table. Further, lock out times can be provided that set the minimum time between doses. For example, if the lock out time is set at one hour and an optional dose is taken, then the next dose would not be available until after an hour of taking that optional dose. Information can also be provided as to the number of tablets or capsules dispense for each dose or optional dose requested. Also, the time interval between optional doses can be provided in the Script table.

Figure 13:
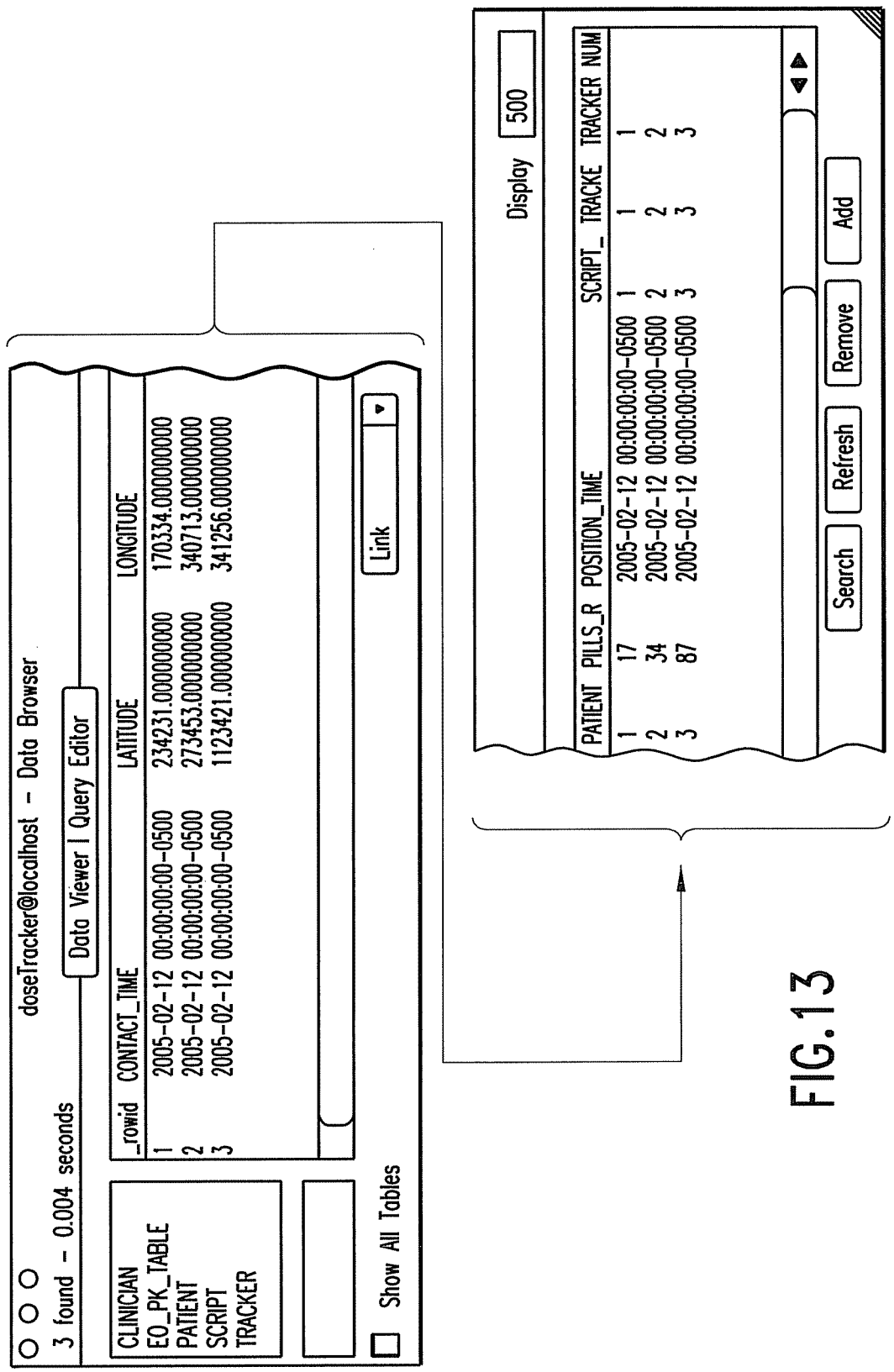
FIG. 13 illustrates a screen of a database that employs the data tables of FIG. 6.

FIG. 13 illustrates a tracker table which identifies the row ID and contact time. The contact time provided is the last time the dispenser had contact with the database to exchange information. The tracker table shows the longitude and latitude of each tracker whose information is contained within the data field. The tracker table also provides columns for the patient ID for the patient and the number of pills remaining. The position time in which the position of each dispenser was last communicated to the database is also provided. The script ID links the dispenser to its prescription. Tracker ID for each dispenser as well as a tracker number and script ID are provided within the tracker table for each dispenser. The tracker table can comprise other information, including dose history that can have a text summary of the times and status of each dose. The dose history of optional doses can be comprised as well. Further, information as to the time of the last dose dispensing and time of the last optional dose dispensing can also be comprised in the tracker table or other tables.

As stated above, different database structures can be used with different information being provided. For example, database structures such as hierarchical models, network models, relational models, object models, relational-object models, or the like, can be used. Further, while database 72 is shown at a remote facility, database 72 can also be stored on the memory of the controller of the system, if the controller has a large enough capacity.

The clinicians in the form of doctors and/or pharmacists, as well as the medication system administrator can have access to various tables within the database. Further, the patient can have limited access to certain information contained within the database. The clinicians, doctors, pharmacists, administrators and patients can have access to the database through an internet web browser interface as previously discussed. The browser based web interface can be provided by an Apple G 5 server or in the Apache web server with web objects acting on the application server. Such Internet web browser interfaces essentially make the central database accessible to users and to controllers on the dispensers through the Internet.

FIGS. 14 through 23 illustrate embodiments of screen shots which a user would encounter through an Internet web browser interface. In particular, the screen shots illustrate screens that would be seen by an administrative level user progressing through the database. FIG. 14 illustrates a login screen which requires the input of a user name and password. An assistant box can be checked in order to identify the person logging into the system as an assistant. Once the user name and password have been entered, the user can click on the login button. This login screen provides a secure access to the data to authorized individuals.

FIG. 15 shows a next level screen that provides access to the different data tables to the administrator user. In particular, FIG. 15 shows a web search page that can be accessed from any web browser. For example, the administrator user can gain access to the clinician table, the patient table, the script table, or the tracker table from this page. The administrator user can look up specific data by using the scroll mechanism provided to look up the different fields within each data table. For example, the user can look up information by last name for the clinician or patient by entering in the specific last name for the clinician or the patient on which the user is trying to retrieve information. Further, the user may be able to find information within the script table. For example, the user can look up information in the field for medication within the script table. Another example can be to look up information within the tracker table related to a certain tracker number by entering the tracker number within the space provided in the cell for the tracker table. Each field within each different table can be searched in this manner. The scroll button beside the field enter cell allows the user to scroll through the different fields. Further, the relationship of what you are trying to search can also be changed. Instead of having information pulled up for the clinician's last name, the "equal sign" can be changed to a "not equal sign", thereby pulling up information on every clinician that does not have the specified last name. In this manner, a variety of ways of searching the different tables within the database can be accomplished through the web browser.

Once in the data table, links can be followed to other related tables. At each level, data editing is possible. Different levels of access can be provided for each type of user. Doctors can only see their own patients listed. Similarly, pharmacies would only see information on their customers listed. Doctors would be allowed to modify their own patients dosing schedule but no add patients or prescriptions. Similarly, pharmacies would be able to add prescriptions but not modify them. If dispensing units are distributed from a central location, only administrators would need to add patients, clinicians, or dispensers to the database. Privileges to add or modify data entries could be assigned to fit individuals. FIGS. 16 through 23 illustrate different information that could be edited within the different tables by an administrative user.

No screen for controller to server communications is illustrated since these communications occur using machine-to-machine protocols. Simple object access protocol ("SOAP") calls are used to exchange XML packets between the dispensers and the database server. Contacts are initiated by the controllers of the dispensers when needed or at timed intervals. The controllers transmit their status of the dispensers and can accept new programming or data (including fingerprint templates for new users). As is evident from the screen shot of the dispensers (trackers data) in FIG. 21, position information is also transmitted. This would allow recovery of lost or stolen units.

FIGS. 24A-32C illustrate another embodiment of a dispenser device, generally designated 300 that can use a pair of slides 340, 350 disposed within a dispensing well 320 of dispenser device 300 to dispense units of medication, such as capsules, tablets, or the like. First slide 340 that can be the top slide when dispenser device 300 is oriented in its upright position can have an opening 342, or aperture, shaped to center and orient the units of medication M in a lengthwise direction so the units drop into an opening 352, or slot, on second slide 350 that can be considered the bottom slide. First slide 340 can have angled sides 344A, 344B at opening 342 in first slide 340 (see FIGS. 29 and 32A-32C) so that extra units of medication that fall therein can be lifted and pushed away from the opening 342 in first slide 340 to prevent jamming.

Second slide 350 can have sides 354 with an angled front side that forms a front ramp surface 354A (see FIGS. 30 and 32A-32C). If two or more units of medication fall into opening 352 in second slide 350 lengthwise, the units of medication can be slid out of this opening 352 in second slide 350 without jamming or being crushed. Further, second slide 350 can have a shutter 356 therein that opens only when second slide 350 is moved to a position where opening 352 in second slide 350 is aligned with opening 322 in dispensing well 320 and/or covered by first slide 340.

In some embodiments, second slide 350 can move in lateral directions to the direction of flow of units of medication through the dispenser device 300. In some embodiments, first slide 340 and second slide 350 can move in lateral directions to the direction of flow of units of medication through the dispenser device 300. In such embodiments, when first slide 340 and second slide 350 are moving, first slide 340 and second slide 350 can move in opposite directions. The use of two counter-moving slides 340, 350 with opening, or apertures, 342, 352 therein and shutter 356 that can cover opening 352 in second slide 350 when the second slide 350 is in specific positions can minimize the lateral movement and the length of first slide 340 and second slide 350. In such embodiments, slide travel distance can be less than 1.5 times the length of the units of medication being dispensed. Further, openings 342, 352 in first and second slides 340, 350 can be self-clearing and can allow a range of sizes of units of medication, such as different sized capsules or pills to be used in a single set of slides 340, 350, especially second slide 350. For example, it is theorized that as few as six opening, or aperture, sizes can accommodate a full range of common tablet and capsule sizes. Dispenser device 300 can allow second slide 350 to be easily switched out to adjust dispenser device 300 to different tablets or capsules.

Upon shifting of first slide 340 and second slide 350 and the moving of shutter 356 to an open position, a unit of medication is dropped into a dispensing chute 370 (see, for example, 32A). A bottom slide door 324 can be opened to access the unit of medication through an opening 322 in dispensing well 320 in dispenser device 300. Door 324 can be manually operated. A detector, such as optical sensor array, 370A in dispensing chute 370 can be used to detect the presence of a unit of medication (see FIGS. 32A-32C). Optical sensor 370A can be used to confirm dispensing and removal of the medication. In practice, not every cycle of lateral movement of slides 340, 350 needs to dispense medication. Some cycles may only clear jams. The slides 340, 350 can cycle until a unit of medication is detected in dispensing chute 370. The state of slide door 324 (opened or closed) can also be detected by a detector, such as optical sensor 325 (see FIGS. 32A-32C). This optical sensor 325 can thereby record removal of the medication. Dispenser device 300 and slides 340, 350 will not activate if a unit of medication is in dispensing chute 370 or if door 324 is open. User interfaces in dispenser device 300 can be simplified. In some embodiments as shown in FIGS. 24A-32C, the LCD screen may not be present. Interfaces, such as controls 318 and LEDs 319, may be used instead. A controller 310 (see FIG. 24C) can be used in dispenser device 300 to controller the movement of first slide 340 and second slide 350 and can be used to provide other information and analysis. Such a controller 310 can be programmed via USB port 312, or by the cell-modem. The embodiments shown in FIGS. 24A-32C are explained in more detail below.

FIGS. 24A-32C show dispenser device 300 for controlling the dispensing of medication. Dispenser device 300 can be used in a system such as system 10 as explained in detail with reference to FIG. 1 above. For example, dispenser device 300 can be used in replace of dispenser 20 in such a system. Therefore, since it is explained above, such a system is not greatly detailed hereinbelow. Rather, dispenser device 300 is more thoroughly described.

As shown in FIGS. 24A-24D, dispenser device 300 can comprise a housing 302 for storing units of medication. For example, housing 302 can comprise different sections 304, 306, 308 that can be held together, for instance, by internal fasteners, such as screws, or by adhesives or other bonding material. Housing 302 can internally contain a controller 310 similar to those described above. Controller 310 can be operatively connected to housing 302. For example, controller 310 can be located in, for example, rear section 304 and can be reside within the interior of housing 302. Rear section 304 of housing 302 can house other components as well, such as motors and wiring.

Controller 310 can control the operations of dispenser device 300 to control and monitor the dispensing of units of medication such as capsules, tablets or other forms of pills. Controller 310 can be programmable with a medication dispensing program. The medication dispensing program can comprise a data store that can contain data important to the dosing and dispensing of medication to a patient. For example, the data store can be comprise a predetermined time to operate the dispenser, the name of the at least one medication, patient data, a patient compliance schedule, pharmacy data, physician data, insurance data, emergency contact data, caregiver data, compliance notification data, or the like. Alternatively, the controller can be programmable to connect to a predetermined Internet service provider through an electronic communication device when dispenser device 300 is used in a system, or a similar system, as shown in FIG. 1. While dispenser device 300 can be a part of a system in some embodiments, dispenser device 300 can be used as a stand-alone device for controlling the dosing of medication as well.

For example, as above, dispenser device 300 can further comprise a communication device 312 that can also be in operable communication with controller 310. Communication device 312 can be a wireless communication device. Similar to the system embodiment shown in FIG. 1, such an electronic communication device 312 can operate on a wireless platform and can comprise an antenna that transmits signals through a cellular network to a remote facility, or location that can house a database for use in controlling dispenser device 300. The database can be accessed by the patient's doctor, pharmacy, and/or administrator of the medication regimen, as well as the patient. Through the wireless connection, controller 310 can communicate through an Internet Service Provider with the database at the remote facility. The Internet Service Provider can manage data collection and distribution to and from the database for the users. The users can comprise the patient, the patient's doctor and/or pharmacist, and/or the administrator of the medication regimen.

Through the internet, appropriate individuals can gain access to the information provided to and from dispenser device 300 to monitor and control the dosing of the medication. For example, such individuals or locations can comprise the patient, the doctor's office, the pharmacy, or the administration facility, where an administrator resides. Authorized personnel from the doctor's office can gain access to patient and dispenser device information stored on the database through a clinician browser. Authorized personnel from the pharmacy can gain access to patient prescription information stored on the database through a pharmacist browser. Authorized personnel from the administration facility can gain access to clinician, pharmacist, and dispenser information stored on database through an administrator browser. Data stored can comprise information such as predetermined times to operate dispenser device 300. The data can also comprise the name of the medication being distributed, the patient's data, the patient's compliance schedule, caregiver data, and compliance notification data as well as pharmacy data, physician data, insurance data, and emergency contact data. Further, such information can be provided on a data store connected to controller 310 within dispenser device 300 itself.

Figure 24A:
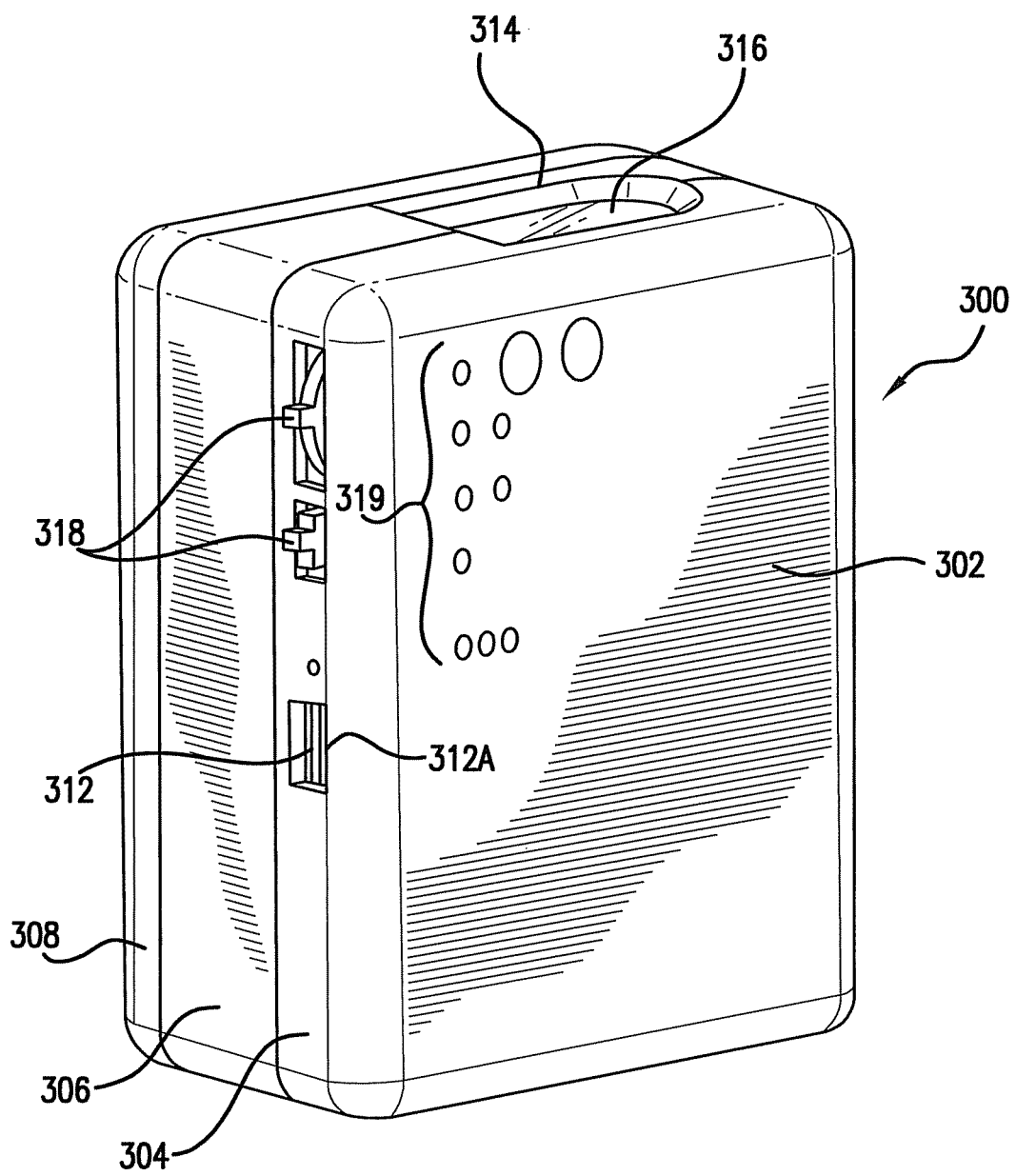
FIGS. 24A and 24B illustrate perspective views of another embodiment of a dispenser device according to the present subject matter.
Figure 24B:
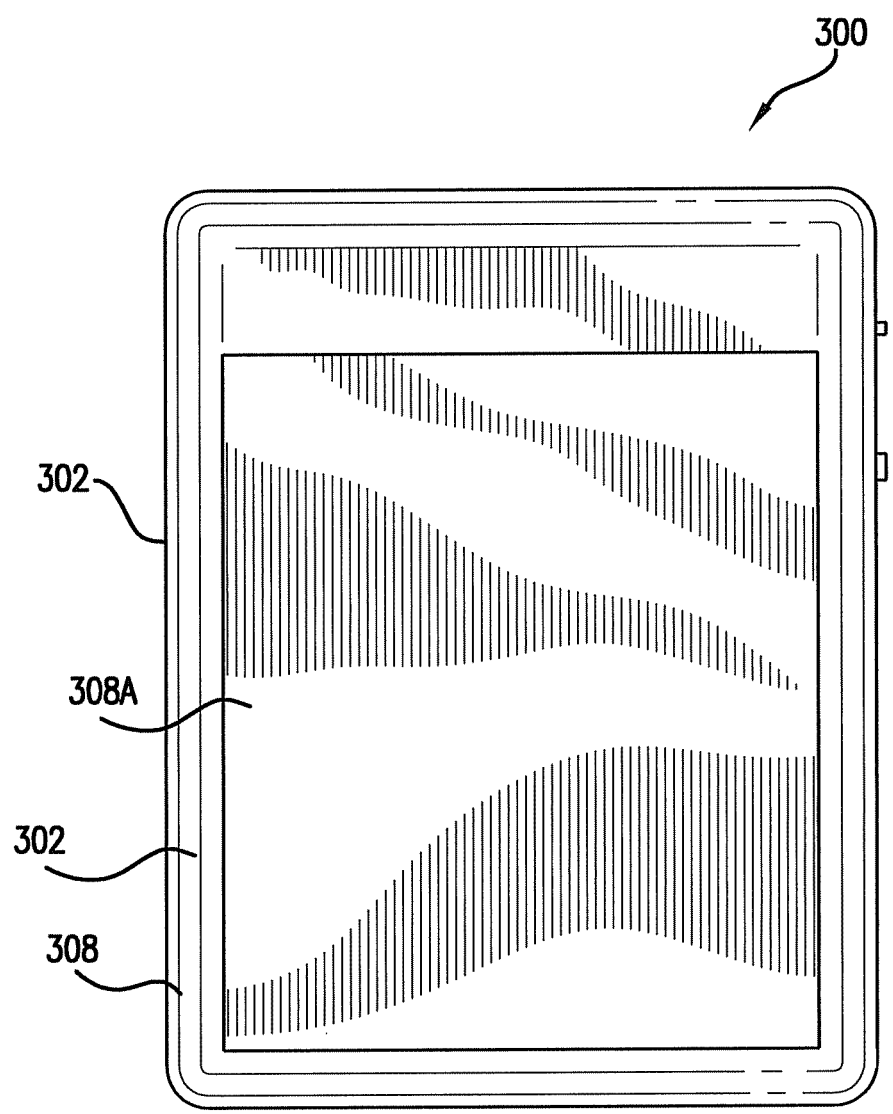
Figure 24C:
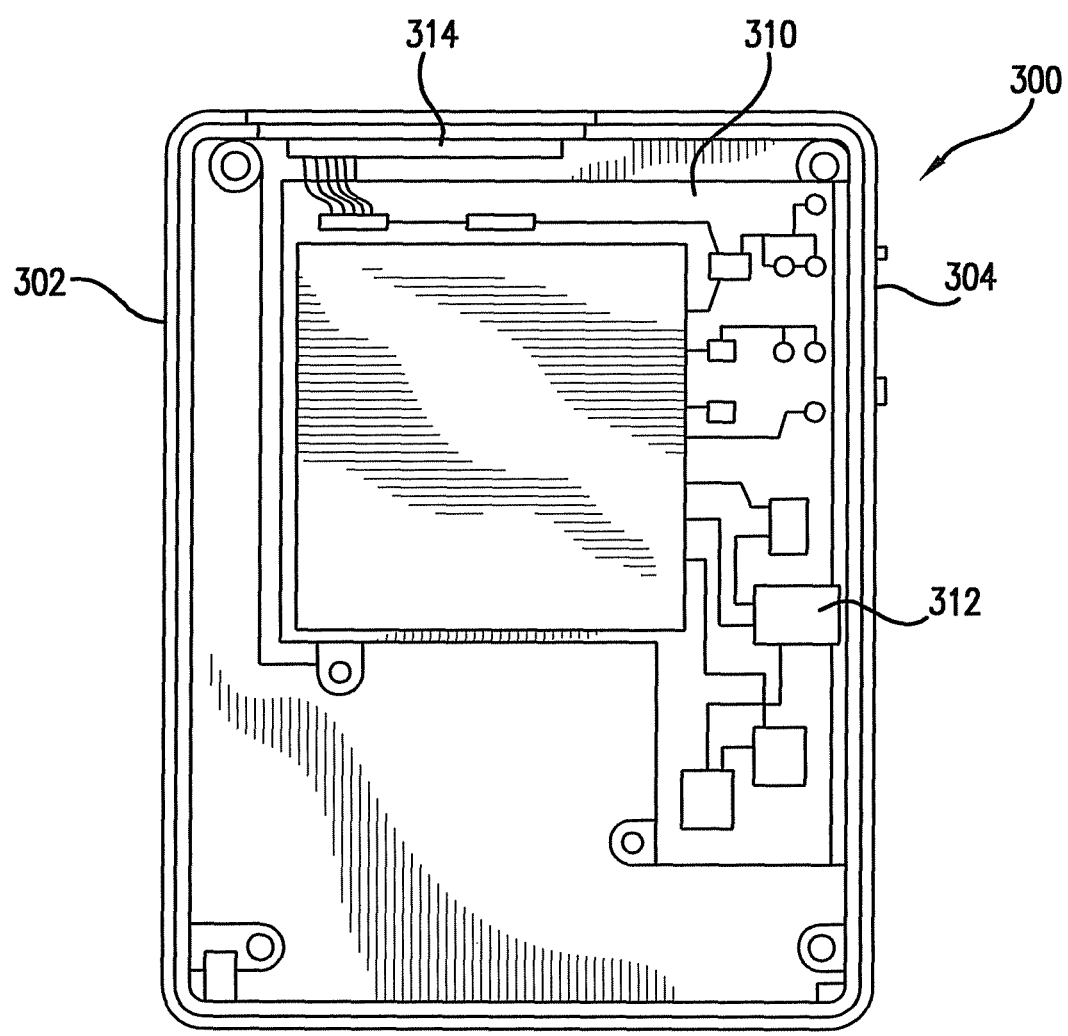
FIG. 24C illustrates a schematic view of an interior portion of the dispenser device according to FIG. 24A.

In such an embodiment as shown in FIGS. 24A and 24C, the controller 310 that can be used in the dispenser device 300 can comprise USB port 312, or a cell-modem. Through the USB port 312 or cell modem, dispenser device 300 can be physically connected to other controller or computing devices such as a wireless modem, a personal computer that may or may not have internet access, a PDA, or the like. Also, controller 310 used in dispenser device 300 can be programmed via USB port 312, or by the cell-modem. In the embodiment shown, USB port 312 can be accessed through rear section 304 of housing 302 through opening 312A. Dispenser device 300 can also comprise an identification verification device for controlling access to the system. For example, the identification verification device can be a biometric identification fingerprint system 314. The fingerprint system 314 can be in communication with controller 310 to verify the identity of the patient. For instance, fingerprint system 314 can comprise a touch screen 316 that can provide a place for the patient to place a finger. Fingerprint system 314 can then read the fingerprint and compare it to stored data to confirm that the individual trying to receive the doses of medication is in fact the intended recipient. As above, other types of identity verification devices can be used in dispenser device 300.

Additionally, as above, the dispenser device 300 can comprise a location determination device for determining the location of the dispenser such as an integrated Global Positioning System (GPS) receiver. Further, the dispenser device 300 can comprise a lockout for disabling functionality of the dispenser device 300 based upon a predetermined criteria. As above, the lockout can comprise a breath sensor for determining a breath alcohol level and the predetermined criteria can comprise a maximum breath alcohol level. Alternatively, and if a display screen is employed by the dispenser device 300, the lockout can comprise an interactive cognitive test and the predetermined criteria can comprise a minimum cognitive level.

As shown in FIG. 24A, manually operated controls 318, such as an on/off switch or the like, can be accessed through the rear section 304 of housing 302. These controls 318 can be in communication with the controller 310 in the housing 302. While a display screen can be used in such an embodiment as dispenser device 300, a less complex communication device can be used to communicate the state and operation of the dispenser device 300. For example, in the embodiment shown in FIG. 24A, lighting devices such as light-emitting diodes (LEDs) 319 can be used to indicate a range of information about dispenser device 300. For instance, LEDs 319 can be used to indicate such information as whether dispenser device 300 is in operation, where the identity of the patient has be verified, whether a unit of medication has been dispensed, when it is time for the patient to take a dose of medication, when dispenser device 300 is low or out of medication, or the other such like information. Such information can be communication to the patient by the specific LEDs that are lit by the controller 310. Sensors within the dispenser device 300 can be in communication with the controller 310 to provide the necessary information to the controller 310 for the controller 310 to light the necessary LEDs 319 to communicate such information. The pattern and number of LEDs 319 and the pattern of lighting of such LEDs 319 to communicate specific information is not dependent on any specific criteria and can be determined by the designer or programmer of the controller 310.

Figure 24D:
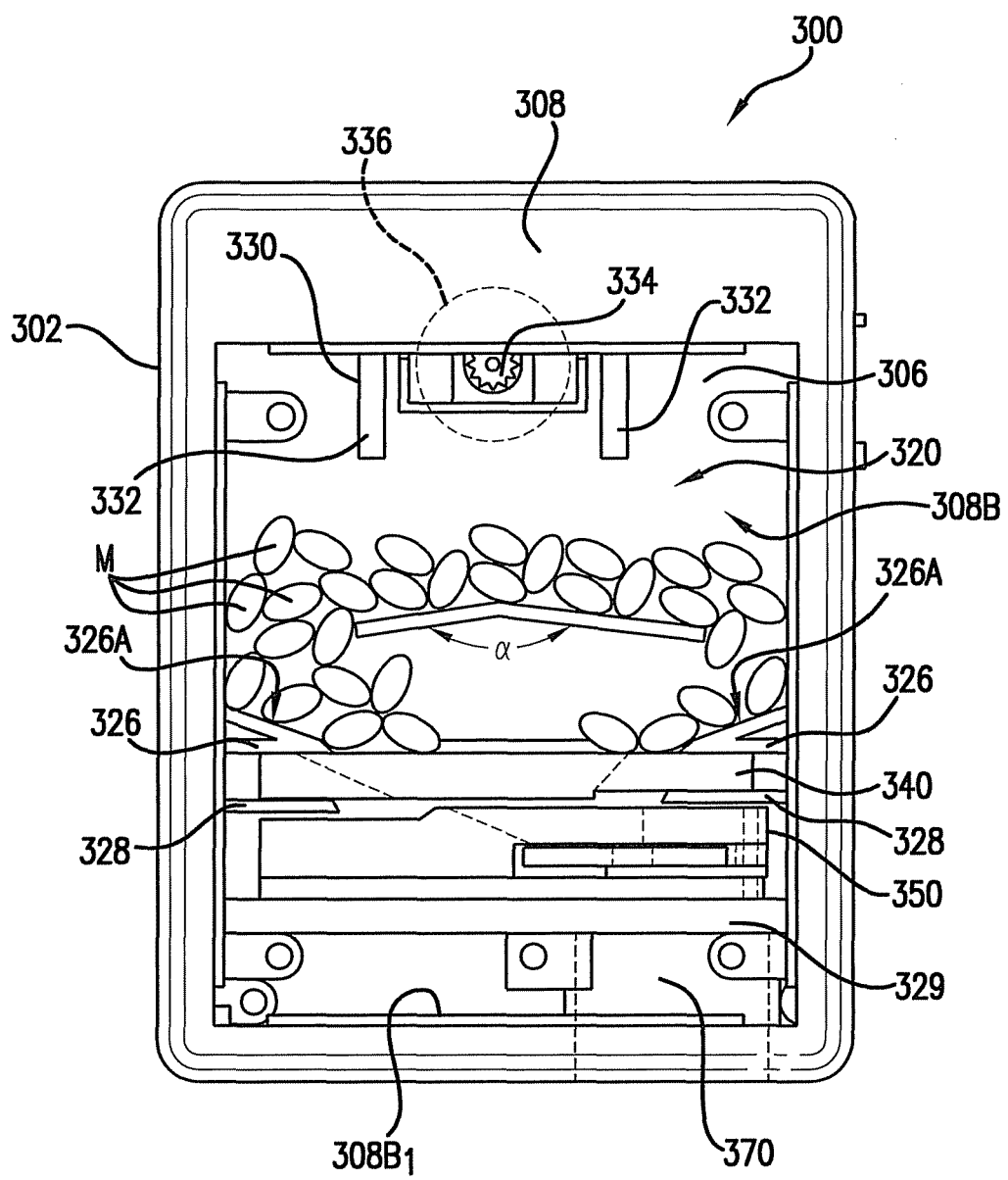
FIG. 24D illustrates a side perspective view of another interior portion of the dispenser device according to FIG. 24A.

As shown in FIG. 24D, housing 302 of dispenser device 300 can comprise a dispensing well 320 that can be used to house units of medication M within the dispenser device 300 that are to be distributed to a patient at predetermined times over a specified period. For example, a one month supply of medication may be placed in dispensing well 320. Once the dispenser device 300 and dispensing well 320 are closed, controller 310 can be used to ensure that the patient does have accessed to the medication, except at predetermined times to facilitate proper dosage and can also monitor compliance of the patient with the dosing schedule as described in detail above. How controller 310 and dispenser device 300 are used to provide proper dosage to the patient is described in more detail below.

In the embodiment shown, front section 308 and middle section 306 of housing 302 can comprise dispensing well 320. As shown in FIG. 24B, front section 308 can comprise a fill door 308A that can be opened to permit filling of dispensing well 320 and closed to deny access into dispensing well 320. FIG. 24D shows section 308 with fill door 308A removed. It is to be noted that fill door 308A can be hingedly attached to housing 302 in some embodiments. Dispensing well 320 of dispenser device 300 can be filled at a pharmacy through an opening 308B vacated by fill door 308A. Fill door 308A can be locked to prevent access to the store of units of medication M within dispensing well 320. A tamper switch, as described above, that is in communication in controller 310 can also be provided to monitor and record the opening of fill door 308A or other tampering that can occur to fill door 308A once dispenser device 300 has left the pharmacy.

Figure 25:
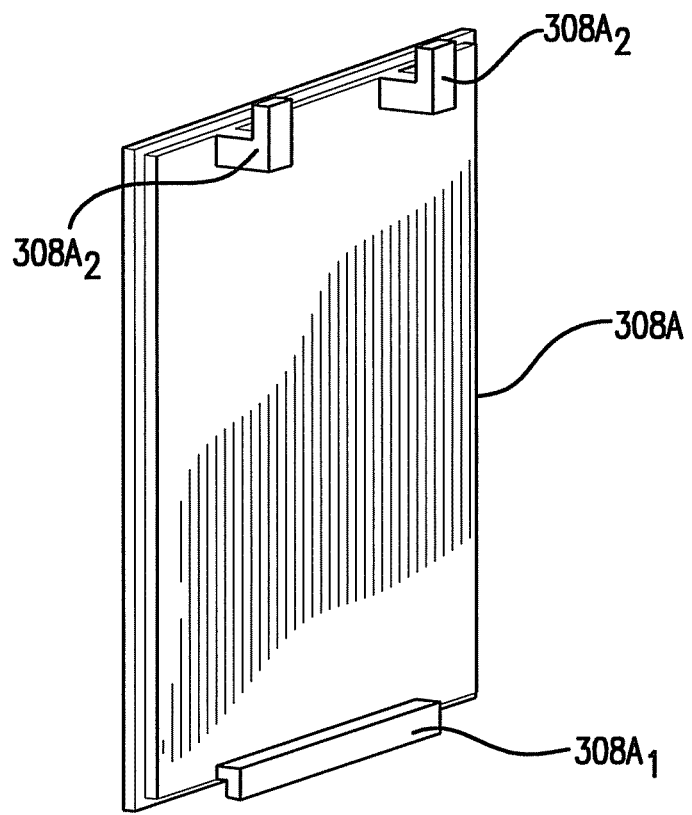
FIG. 25 illustrates a perspective view of an embodiment of a fill door that can be used in the dispenser device according to FIG. 24A.
Figure 26:
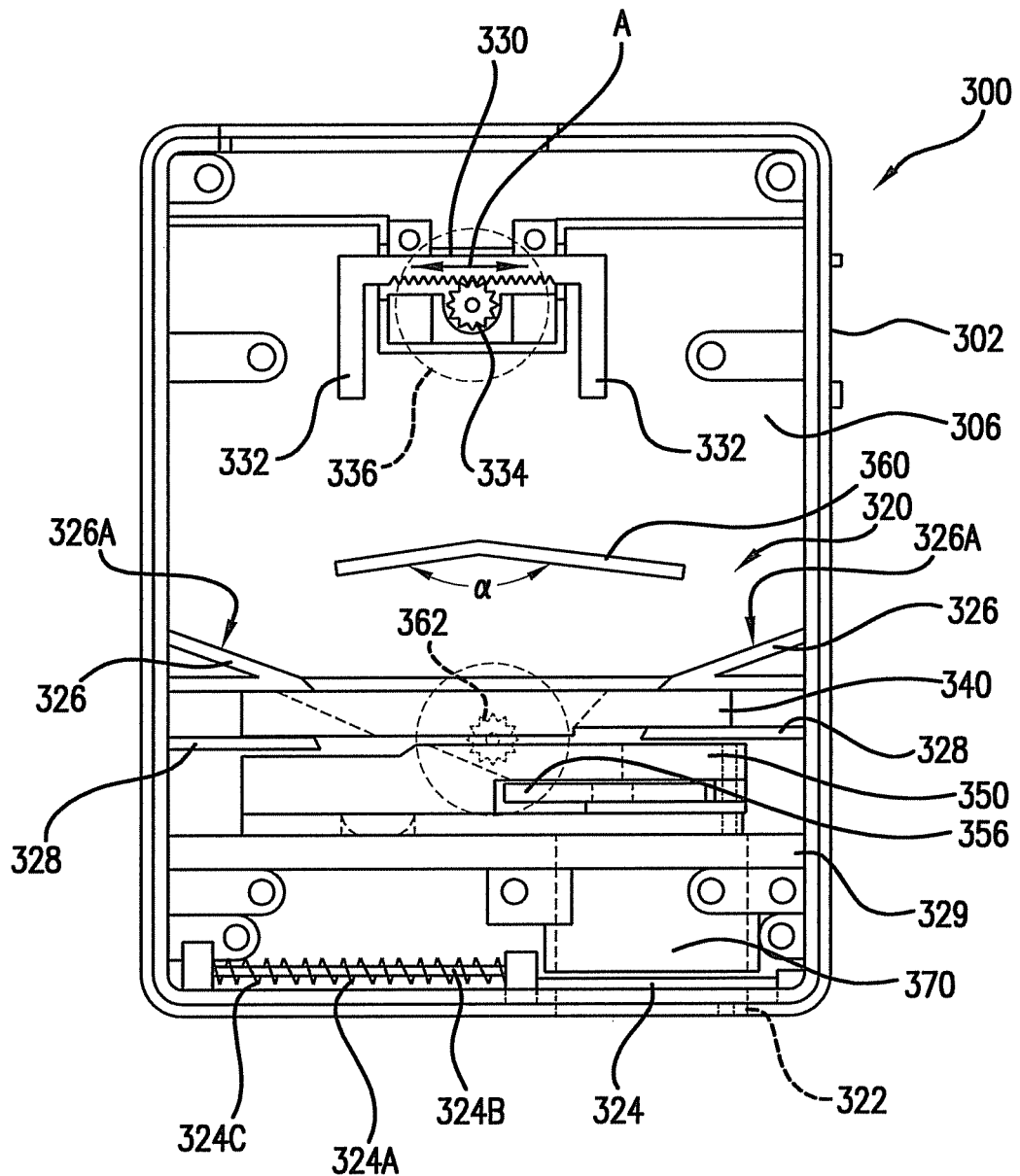
FIG. 26 illustrates schematic view of a further interior portion of the dispenser device according to FIG. 24A.

As shown in FIG. 25, fill door 308A can comprise latches 308A$_2$ that can be engaged to lock fill door 308A in a closed position. In the embodiment shown, fill door 308A comprises bottom latches 308A$_1$ that can engage a lower edge 308B$_1$ of the portion of front section 308 that defines the opening 308B through which dispensing well 320 can be filled. Upper latches 308A$_2$ can be engaged by a rack 330 (see FIGS. 24D and 26) that can lock fill door 308A closed. In particular, rack 330 can have extension arms 332 that extend downward to engage upper latches 308A$_2$ of fill door 308A once it is placed in a closed position. As shown in FIG. 26, extension arms 332 can have an angled, or ramped, back surface to facilitate engagement of upper latches 308A$_2$ and movement of the extension arms 332 into the locking position. Additionally or alternatively, upper latches 308A$_2$ can have a similar matching angled, or ramped, surface.

Rack 330 can have teeth therein that can engage a pinion gear 334 that is driven by a motor 336. As pinion gear 334 rotates the rack 330 is moved in transverse directions A. For example, in the embodiment shown, if pinion gear 334 is rotated in a clockwise direction as viewed in FIG. 26, the rack 330 and extension arms 332 will move laterally in a direction to the left to a closed or locked position. If pinion gear 334 is rotated in a counter-clockwise direction as viewed in FIG. 26, the rack 330 and extension arms 332 will move laterally in a direction to the right to an open or unlocked position. Thus, dispensing well 320 can comprise a rack 330 and pinion 334 therein with the rack 330 being movable in transverse directions to engage with latches 308A$_2$ of fill door 308A to lock fill door 308A and to unengaged latches 308A$_2$ of fill door 308A to unlock the fill door 308A.

Figure 27:
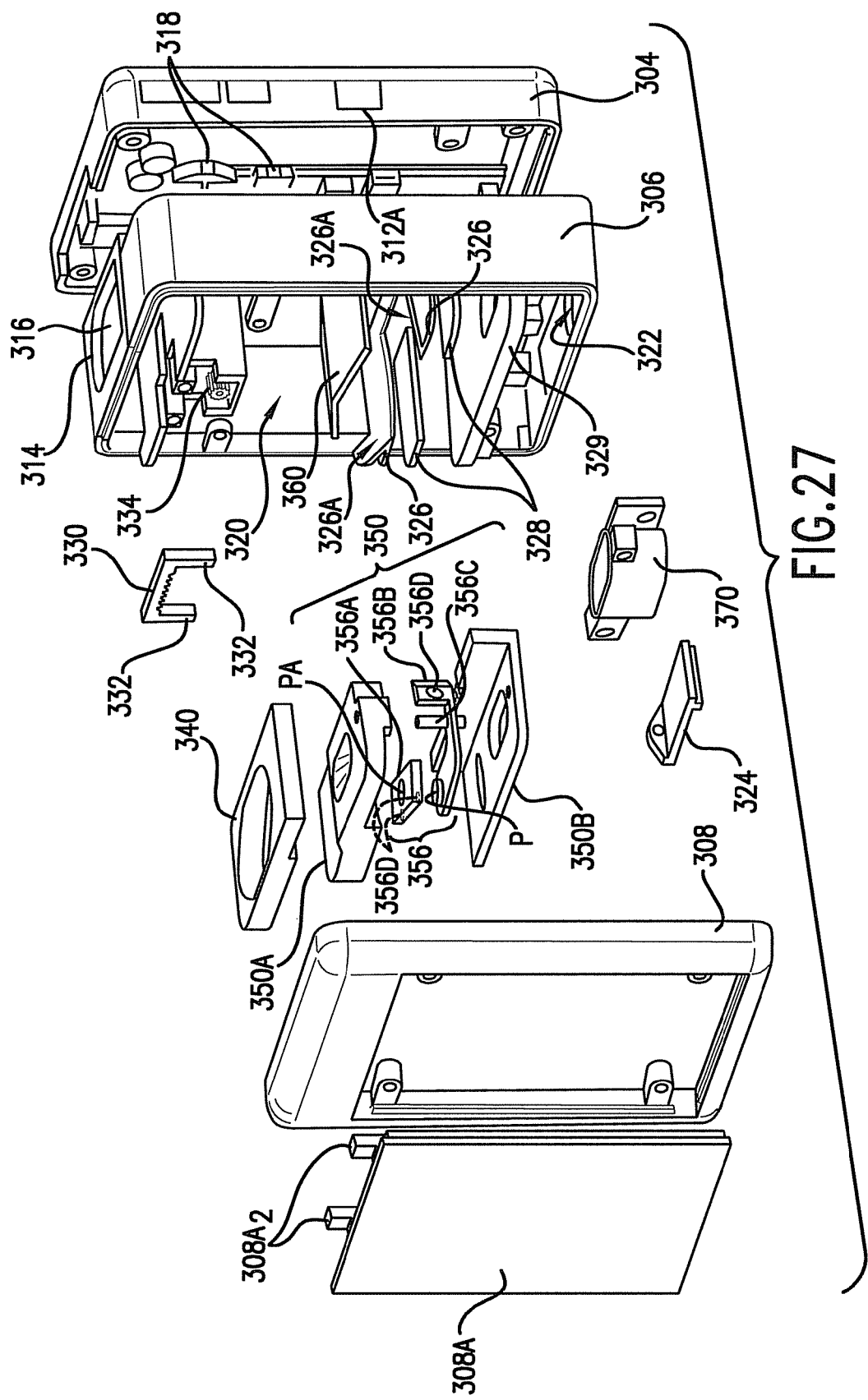
FIG. 27 illustrates an exploded view of a portion of the dispenser device according to FIG. 24A.
Figure 28:
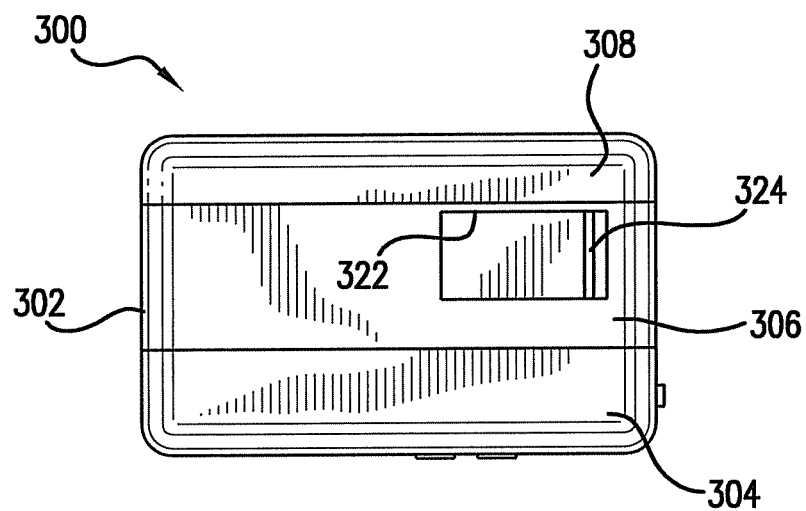
FIG. 28 illustrates a bottom view of a portion of the dispenser device according to FIG. 24A.

Components used to dispense units of medication M from dispenser device 300 will now be described in detail. Dispensing well 320 has an opening 322 therein to permit removal of units of medication M therefrom as seen in FIGS. 26-28. Opening 322 can be covered by a dispensing door 324 to close opening 322 in dispensing well 320 as shown in FIG. 28. Dispensing door 324 can be retractable to dispense a unit of medication M from dispensing well 320 once the unit of medication is dispensed to opening 322. Dispensing door 324 can be opened through an automated retraction process. For example, a motor connected to controller 310 can have a screw rod that threadingly engages dispensing door 324 to open and close dispensing door 324 as the screw rod is rotate in the appropriate direction by the motor. Alternatively, dispensing door 324 can be manually retractable. For example, in the embodiment as shown in FIGS. 26 and 32A-32C, dispensing door 324 can engage a biasing element 324A that forces dispensing door 324 into a closed position. Biasing element 324A can comprise a rod 324B and a spring 324C. As shown, dispensing door 324 can engage rod 324B. Spring 324C can reside on rod 324B and bias dispensing door 324 toward a closed position. The patient can push dispensing door 324 back so that dispensing door 324 travels down rod 324B and compresses spring 324C.

To ensure that a single unit of medication is dispensed at a time, a first slide 340 and a second slide 350 can reside in dispensing well 320. Controller 310 can operate first slide 340 and second slide 350 to dispense a unit of medication to opening 322 in dispensing well 320. At least one of these slides 340 and 350 can be laterally moved or shifted to move a unit of medication to a position where it can be accessible through opening 322 in dispensing well 320. First slide 340 can have opening 342 therein that is configured to funnel a unit of medication toward opening 322 in dispensing well 320. Second slide 350 can be disposed between opening 322 in dispensing well 320 and first slide 340. Second slide 350 can have opening 352 therein that is configured to receive a unit of medication. Opening 352 in second slide 350 is alignable with opening 322 in dispensing well 320 and opening 342 in first slide 340.

Such alignments do not necessarily occur simultaneously. In particular, the alignment of opening 352 in second slide 350 with opening 342 in first slide 340 can occur at a different moment and a different location than the alignment of opening 352 in second slide 350 with opening 322 in dispensing well 320 due to the lateral movement of second slide 350 relative to first slide 340 and opening 322 in dispensing well 320. Opening 342 in first slide 340 is configured to funnel a unit of medication to opening 352 in second slide 350 when opening 342 and opening 352 are substantially aligned. Second slide 350 is configured to funnel the unit of medication to opening 322 in dispensing well 320 upon movement of second slide 350 into a position that is aligned with opening 322 in dispensing well 320.

Gravity can be used to facilitate operation of dispenser device 300. Thus, when dispenser device 300 is disposed in its upright position as shown in FIGS. 24A, 24B, and 24D, gravity helps to orient units of medication M for dispensing. To facilitate movement of units of medication M to a position for reception in opening 342 in first slide 340, dispensing well 320 can comprise a ramped surface on either side of first slide 340. For example, dispensing well 320 can comprise a divider 326 that has a ramped surface 326A that funnels units of medication toward opening 342 in first slide 340. The ramped surface 326A can also help to alleviate jamming. Further, dispensing well 320 can comprise other dividers 328, 329 that are used to separate and support first slide 340 and second slide 350. Divider 328 can separate first slide 340 and second slide 350. Divider 328 can provide two sides for supporting first slide 340 and separating first slide 340 and second slide 350 and a wide opening 328A that allows for opening 342 of first slide 340 to be in communication with opening 352 of second slide 350. Divider 329 can support second slide 350 and can extend across the width of dispensing well 320. Divider 329 can have an opening 329A therethrough that is aligned with opening 322 in dispensing well 320. As second slide 350 is moved in a lateral direction toward a position of dispensation for a unit medication residing in opening 352 in second slide 350, opening 352 in second slide 350 can align with opening 329A of divider 329 and opening 322 in dispensing well 320 so that the unit of medication can be dropped to door 324 for dispensing.

A diverter shield 360 can be disposed within dispensing well 320 above the first and second slides 340, 350. Diverter shield 360 can be configured to divert units of medication M that reside above diverter shield 360 and first and second slides 340, 350 to either side of the first slide 340 to reduce the opportunity for jamming as shown in FIG. 24D. To accomplish this, diverter shield 360 can be configured to be angled downward on both sides. For example, diverter shield 360 can be angled at an angle α. To determine when dispensing well 320 is empty of medication, a sensor, such as an optical detector, can be provided in the dispensing well 320.

Figure 29:
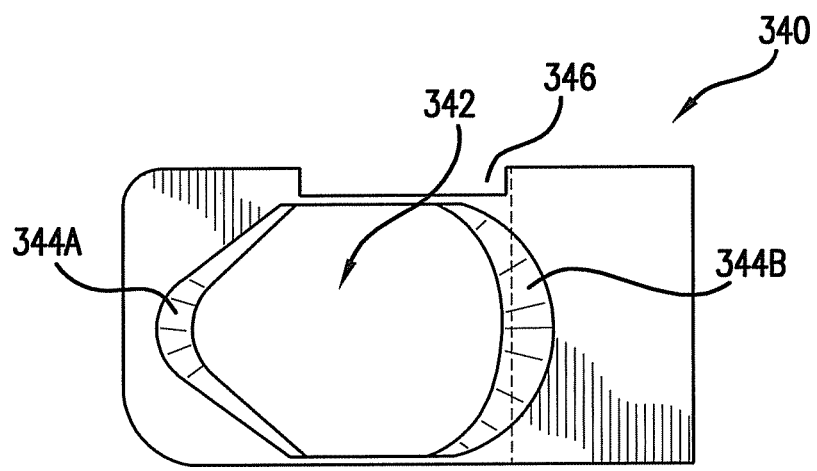
FIG. 29 illustrates a top view of an embodiment of a first slide that can be used in the dispenser device according to FIG. 24A.

As shown in FIGS. 24D and 29, opening 342 in first slide 340 can be configured to receive units of medication M as they are oriented in a lengthwise direction to align and drop a unit of medication into opening 352 in second slide 350. First slide 340 can comprise opposing sides 344A, 344B that define opening 342 therein. Sides 344A, 344B can be angled to funnel and orient units of medication M for feeding to opening 352 in second slide 350 and to prevent jamming.

Figure 30:
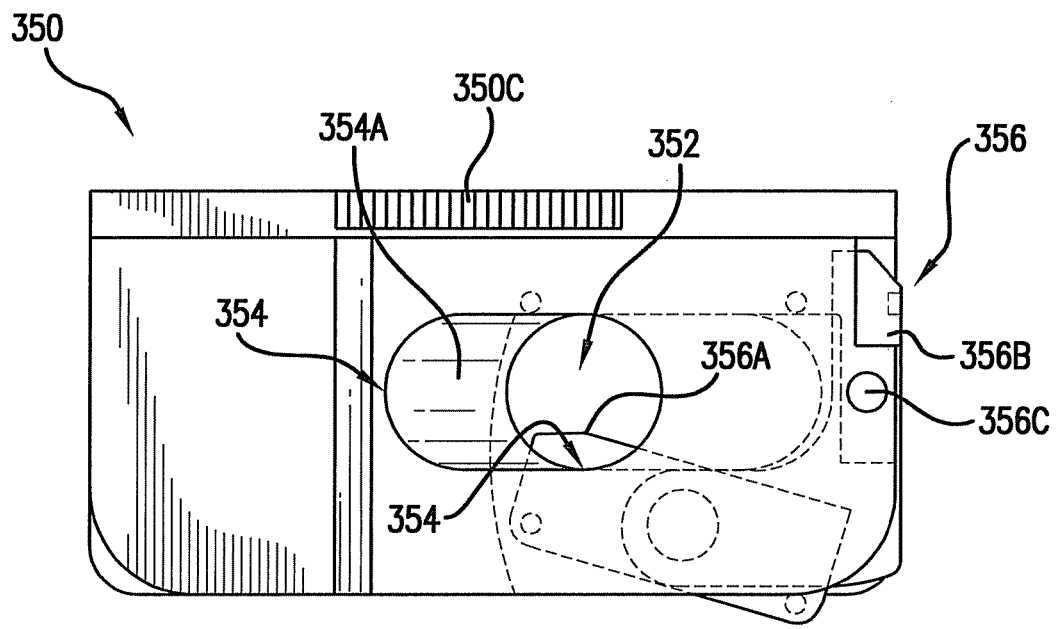
FIG. 30 illustrates a top view of an embodiment of a second slide that can be used in the dispenser device according to FIG. 24A.

Second slide 350 comprises sides 354 that define opening 352 in second slide 350 as shown in FIGS. 24D and 30. Sides 354 can be configured to provide a front ramped surface 354A that works in cooperation with angled sides 344A, 344B of first slide 340 to funnel and orient units of medication M for feeding to opening 322 in dispensing well 320 and to prevent jamming. As mentioned above, shutter 356 can be disposed between second slide 350 and opening 322 in dispensing well 320. Shutter 356 is movable from a closed position with opening 352 in second slide 350 covered by shutter 356 and an open position where opening 352 in second slide 350 is not obstructed by shutter 356 to permit units of medication M to pass through opening 352 in second slide 350 toward opening 322 in dispensing well 320. In some embodiments as shown, second slide 350 can comprise an upper portion 350A and a lower portion 350B with shutter 356 disposed between upper portion 350A and lower portion 350B. Thus, upper portion 350A and lower portion 350B can create a space therebetween for shutter 356 to operate. It is understood, however, that, in some embodiments, shutter 356 can operate at a position below second slide 350 and that, in some embodiments, second slide 350 can be a solitary component.

As shown in FIG. 27, shutter 356 can comprise a shutter blade 356A that can be moved to a closed position in front of opening 352 in second slide 350 to cover opening 352 or at least block passage of a unit of medication disposed therein and to an open position where the shutter blade dose not impede the passage of a unit of medication disposed in opening 352 in second slide 350. The shutter blade 356A can be attached to a lever arm 356B that can be used to move shutter blade 356A from the closed position to the open position and vice versa. The lever arm 356B can be secured to a fulcrum support 356C. For example, lever arm 356B can have an aperture through which fulcrum support 356C can pass. Alternatively, lever arm 356B and fulcrum support 356A can be an integral solitary component. The lever arm 356B can pivot around fulcrum support 356C to move shutter blade 356A. In some embodiments, as shown in the figures, fulcrum support 356C can be attached to one or both of upper portion 350A and lower portion 350B. Similarly, lever arm 356B can engage shutter blade 356A such that shutter blade 356A pivots on lever arm 356B. For example, lever arm 356B can comprise a pivot P that can engage a pivot aperture PA in shutter blade 356A. Shutter blade 356A can pivot around pivot P to facilitate movement between the closed and open positions.

Lever arm 356B and shutter blade 356A can be pivoted in different manners. For example, in some embodiments, to also facilitate movement of the shutter blade 356A between the closed and open positions, magnets 356D can be included on at least one of lever arm 356B, shutter blade 356A, or housing 302. For example, a magnet 356D can be included on an end of lever arm 356B distal from shutter blade 356A that can interact with a metal portion or another magnet embedded in the wall of section 306 of housing 302 proximal to lever arm 356B. The magnetic attraction of magnet 356D on the end of lever arm 356B distal from shutter blade 356A can attract and hold that end of lever arm 356B as second slide 350 moves away from the wall of section 306 proximal to lever arm 356B to pivot lever arm 356B causing that end of lever arm 356B to pivot outward from second slide 350 and an end of lever arm 356B on which shutter blade 356A resides to pivot inward toward opening 352 in second slide 350 so that shutter blade 356A can enter the closed position.

As second slide 350 moves toward the wall of section 306 of housing 302 proximal to lever arm 356B, the wall pushes lever arm 356B toward second slide 350 causing an end of lever arm 356B on which shutter blade 356A resides to pivot outward from opening 352 in second slide 350. In this manner, shutter blade 356A move towards the open position. To facilitate movement of shutter blade 356A to the open position, one or more magnets 356D can be included on shutter blade 356A that can interact with a metal portion or another magnet embedded in a wall formed by fill door 308A and/or section 308 of housing 302 proximal to shutter blade 356A. The wall formed by fill door 308A and/or section 308 of housing 302 proximal to shutter blade 356A can help move shutter blade 356A into the open position by providing a structure that will abut against shutter blade 356A to pivot shutter blade 356A so that its side is in generally parallel alignment with that wall formed by fill door 308A and/or section 308. One or more magnets 356D in shutter blade 356A can help align and hold shutter blade 356A in the open position next to the wall formed by fill door 308A and/or section 308.

As stated above, first slide 340 can be movable in a lateral direction. Additionally or alternatively, second slide 350 can be movable in a lateral direction. In some embodiments, second slide 350 can be movable in a lateral direction, while first slide 340 is stationary. For example, second slide 350 can have teeth 350C (see FIG. 30) that engage a gear that moves second slide 350 back and forward in the lateral directions, while first slide 340 does not engage the gear. For example, first slide 340 can have an indention 346 (see FIG. 29) where the gear can operate without moving first slide 340. Thus, first slide 340 can be stationary and fixed or secured to section 306 of housing 302, while second slide 350 is movable. In embodiments where first slide 340 is designed to move in lateral directions, teeth, such as teeth 350C, in second slide 350 shown in FIG. 31, can occupy indention 346 of first slide 340.

Figure 31:
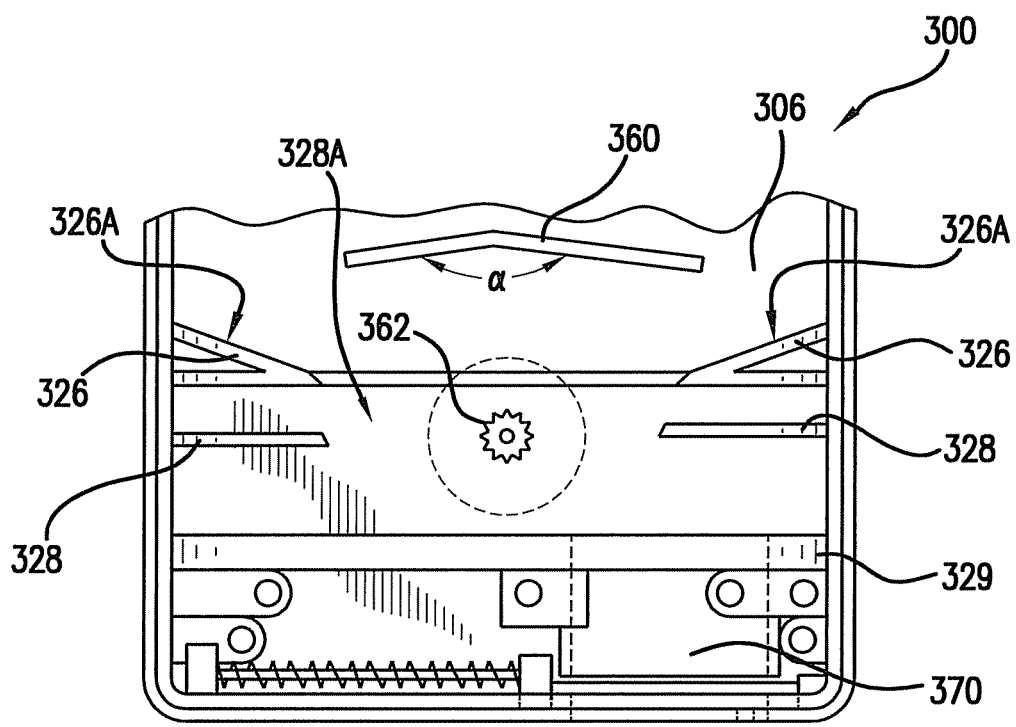
FIG. 31 illustrates an additional side perspective view of a portion of the interior of the dispenser device according to FIG. 24A.

In some embodiments, both first slide 340 and second slide 350 can be movable in lateral directions to facilitate dispensing of a unit of medication M. In such embodiments, first slide 340 can move in a direction counter to the direction in which second slide 350 moves. This can be accomplished by one or more motors that can drive first slide 340 and second slide 350. For example, as shown in FIG. 31, a motor represented by gear 362 can drive either or both first slide 340 and second slide 350 depending on the configuration of first slide 340 and second slide 350. For example, if both first slide 340 and second slide 350 have teeth along a side that can engage gear 362, then as gear 362 is turned by the motor, first slide 340 on top of gear 362 will be driven in one direction, while second slide 350 on bottom of gear 362 will be driven in the opposite direction. If the direction of rotation of gear 362 is reversed by the motor, then first slide 340 and second slide 350 will be driven in opposite directions both to each other and to the direction in which the gear 362 had previously driven them. If, for example, teeth are provided by the second slide 350 but not the first slide 340, then only second slide 350 will be driven by gear 362. In such a manner, first slide 340 and second slide 350 can, for example, be movable a distance of less than about 1.5 times the length of the unit of medication M being dispensed.

With the aid of angle sides 344A, 344B of first slide 340 and ramped surface 354A of second slide 350, opening 342 in first slide 340 and opening 352 in second slide 350 are self-clearing through the lateral movement of first slide 340 and second slide 350.

To facilitate the directing of the unit of medication being dispensed from opening 352 in second slide 350 to opening 322 in dispensing well 320, a dispensing chute 370 can be disposed between second slide 350 and opening 322 in dispensing well 320 as shown in FIGS. 24D, 26, 27, and 31-32C. Opening 352 in second slide 350 can be alignable with dispensing chute 370 and opening 322 in dispensing well 320 to provide a unit of medication for dispensing. For example, the dispensing chute 370 can be disposed between divider 329 and dispensing well 320 so that dispensing chute 370 aligns with opening 329A in divider 329 and opening 322 in dispensing well 320. When second slide 350 is moved to a dispensing position, opening 352 in second slide 350 can align with dispensing chute 370, opening 329A in divider 329 and opening 322 in dispensing well 320 to permit a unit of medication in opening 352 in second slide 350 to be dropped to door 324. Door 324 can be disposed between dispensing chute 370 and dispensing well 320 so that door 324 covers opening 322 in dispensing well 320 and breaks communication between dispensing chute 370 and opening 322 when door 324 is in a closed position. When door 324 is opened, dispensing chute 370 and opening 322 in dispensing well 320 can be in communication to permit dispensing of any unit of medication that has been provided by second slide 350.

Figure 32A:
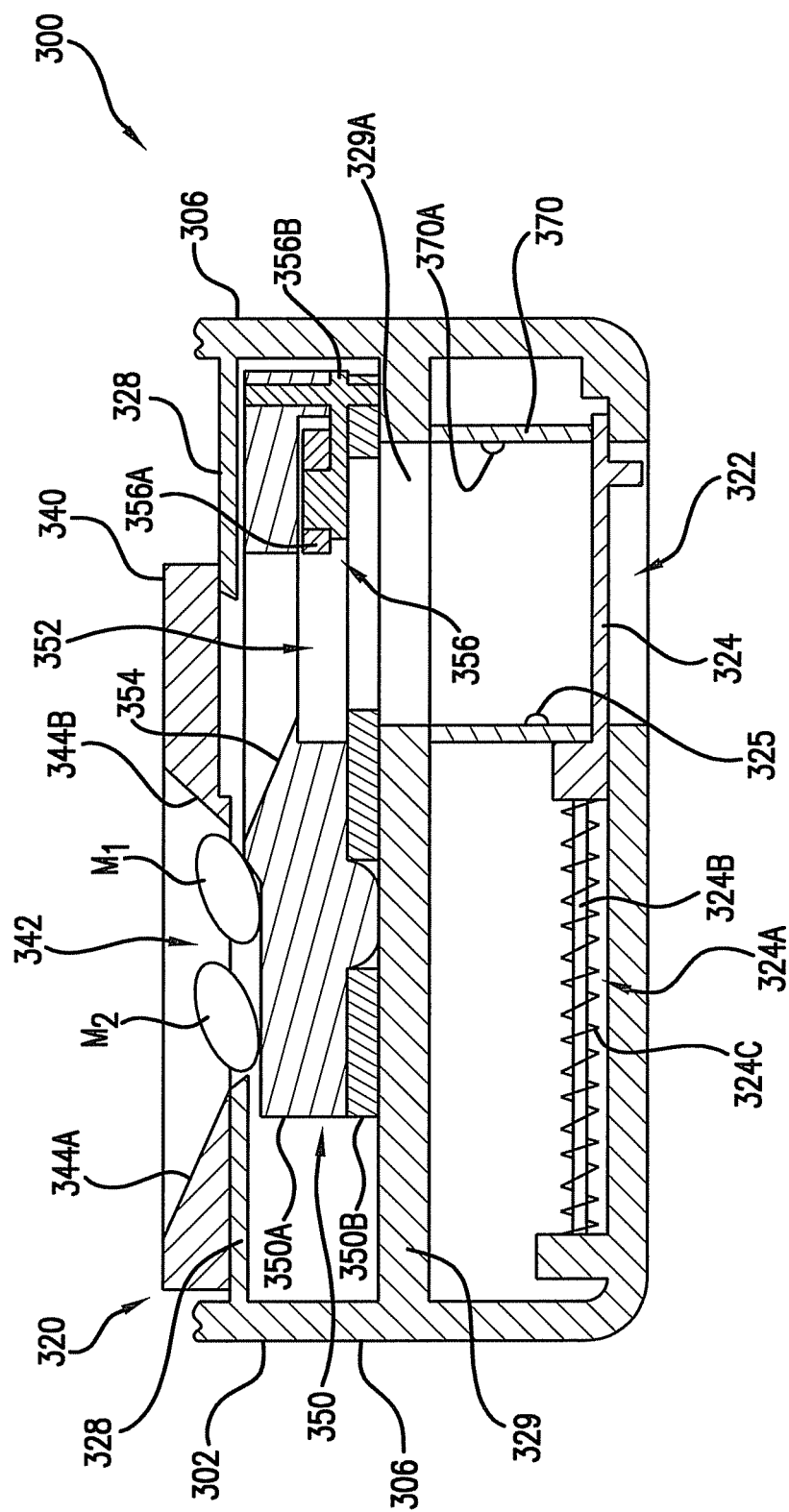
FIGS. 32A-32C illustrate partial cross-sectional side views of the dispenser device according to FIG. 24A illustrating operation of slides therein.
Figure 32B:
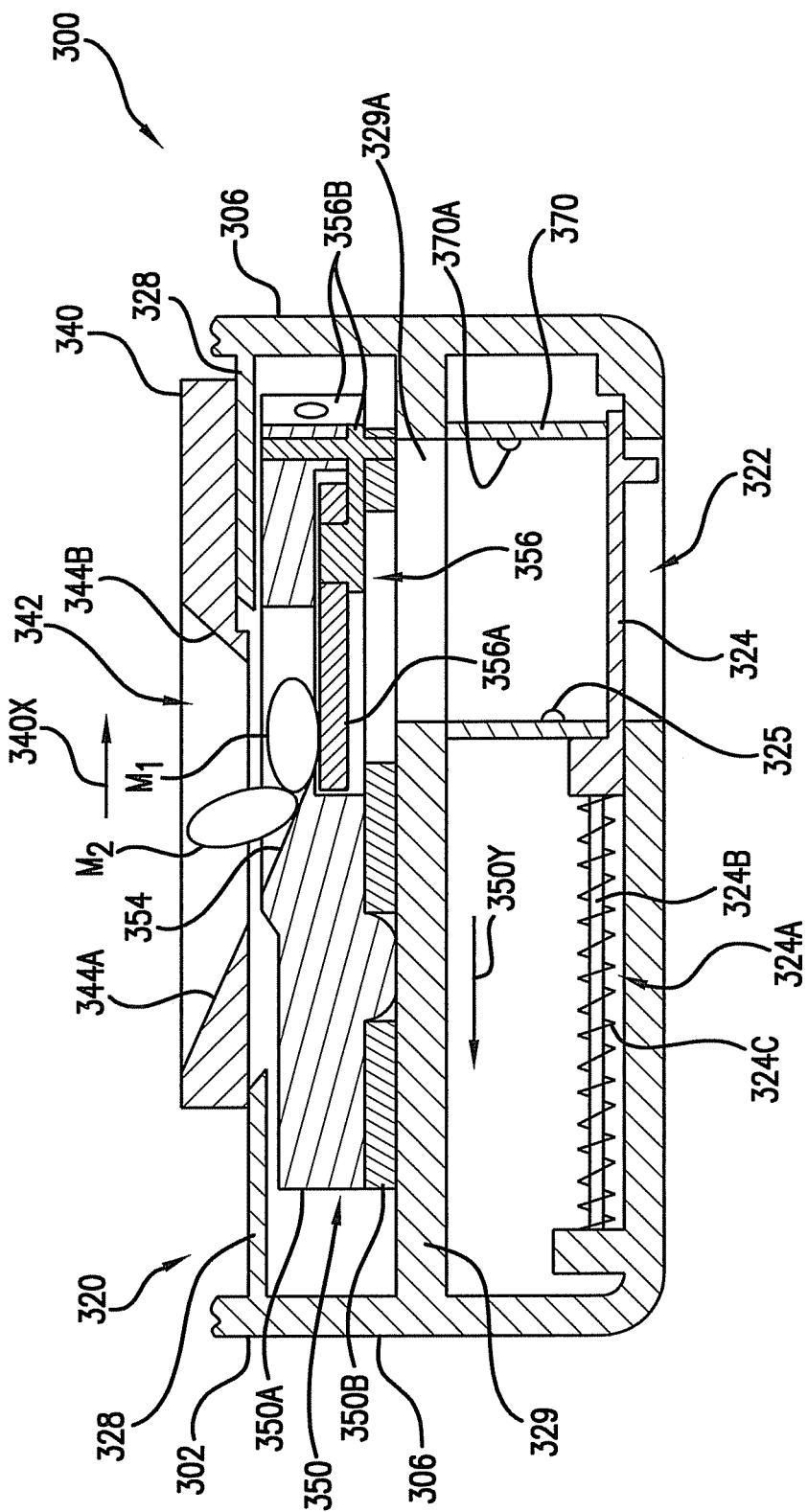
Figure 32C:
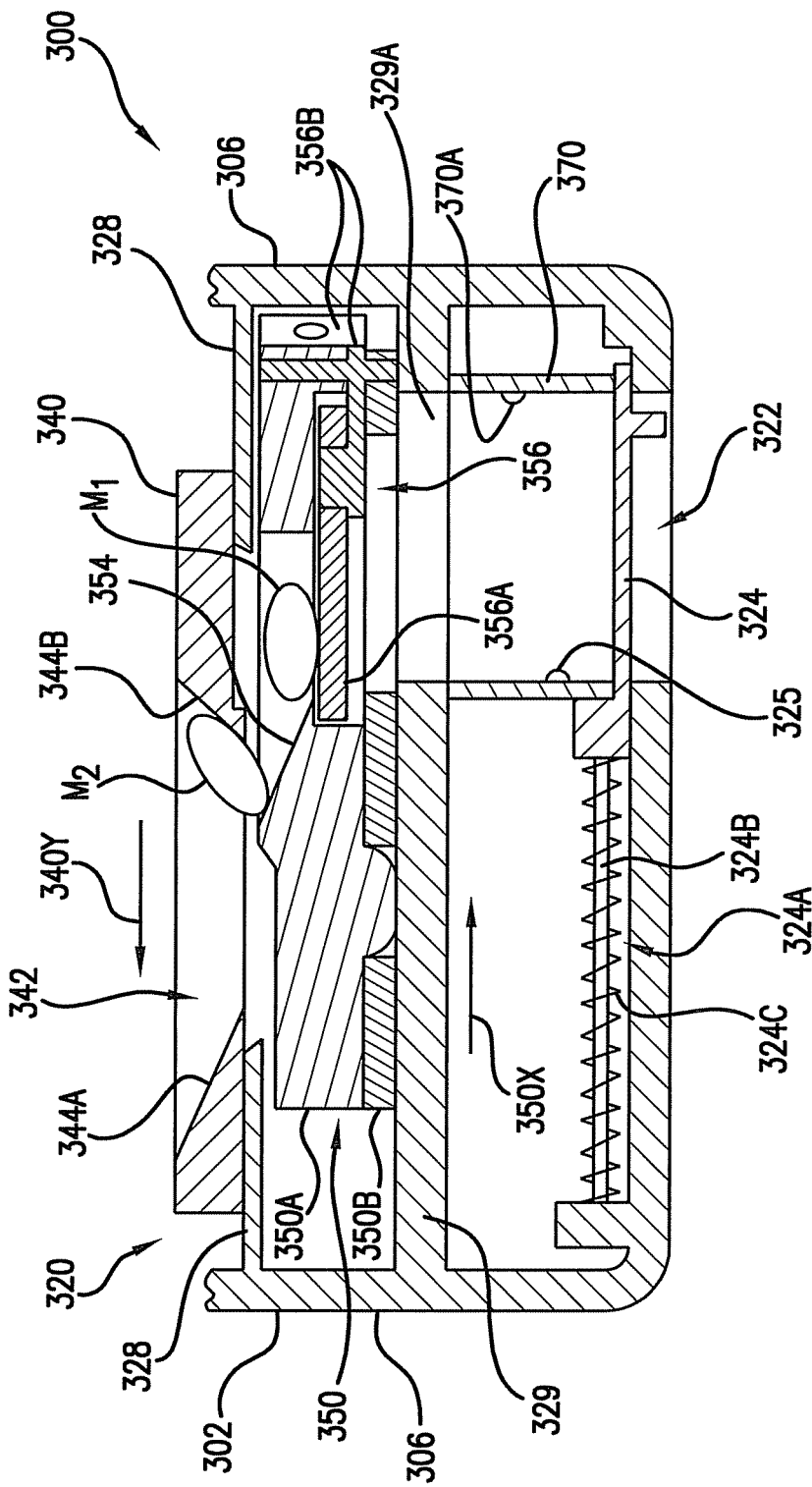

An example of how first slide 340 and second slide 350 can operate together in dispensing well 320 of dispenser device 300 to dispense medication is illustrated in FIGS. 32A-32C. In the embodiment shown, both first slide 340 and second slide 350 can be laterally moved in counter directions. FIG. 32A shows a cross-section of a portion of dispensing well 320 where first and second slides 340, 350 are in a dispensing position where a unit of medication has already been dispensed. First slide 340 is supported above second slide 350 by divider 328. Opening 352 in second slide 350 is aligned with opening 329A in divider 329 and dispensing chute 370.

Thus, a unit of medication that had resided in opening 352 can pass through opening 329A in divider 329 and dispensing chute 370 and can be removed through opening 322 once door 324 is pulled back. Dispensing chute 370 can comprise one or more sensors 370A to detect the presence of a unit of medication in dispensing chute 370 and/or one or more sensors 325 to detect whether door 324 is opened or closed. First slide 340 is in a position where opening 342 in first slide 340 is not aligned with opening 352 in second slide 350 and first slide 340 covers opening 352 in second slide 350. Thus, extra units of medication may not enter opening 352 in second slide 350 when in this dispensing position. Opening 342 in first slide 340 can have one or more units of medication $M_1$, $M_2$ that reside therein and rest on a top surface of second slide 350, but do not have access to opening 352 in second slide 350.

When it is time to dispense a unit of medication, the identity of the patient can be verified by the identification verification device 314 (see FIG. 24A). Controller 310 (see FIG. 24C) can then move first slide 340 and second slide 350 in opposite directions. In particular, controller 310 can active a motor to rotate gear 362 (see FIG. 31) to drive first slide 340 in direction 340X and second slide 350 in direction 350Y to a receiving position for receiving a unit of medication in opening 352 in second slide 350 as shown in FIG. 32B. As shown in FIG. 32B, as second slide 350 moves in direction 350Y, lever arm 356B is pivoted as described above to cause shutter blade 356A of shutter 356 to move into a closed position blocking opening 352 in second slide 350. Opening 352 in second slide 350 can align with opening 342 in first slide 340 so that one or more units of medication $M_1$, $M_2$ that were in opening 342 in first slide 340 can fall or drop into opening 352 in second slide 350 against shutter blade 356A. Angled sides 344A and 344B of opening 342 in first slide 340 can facilitate movement of one or more units of medication $M_1$, $M_2$ toward opening 352 in second slide 350. The size of opening 352 in second slide 350 can be such that a single unit of medication can fit therein. Front ramp surface 354 of second slide 350 can also help position a unit of medication such as unit of medication $M_1$ in opening 352 in second slide 350. Excess units of medication that fall or drop into opening 352 in second slide 350 generally will not completely fit. For example, as shown in FIG. 32B, unit of medication $M_1$ occupies opening 352 in second slide 350 with the excess unit of medication $M_2$ not completely fitting into opening 352 in second slide 350. Such excess units of medication can be removed through movement through movement of first slide 340 and second slide 350 as will be explained below in more detail.

Once first slide 340 and second slide 350 reach the receiving position, controller 310 (see FIG. 24C) can reverse the motor and gear 362 (see FIG. 31) so that first slide 340 and second slide 350 reverse direction of travel. For example, as shown in FIG. 32C, first slide 340 is moved in direction 340Y and second slide 350 is moved in direction 350X towards the dispensing position illustrated in FIG. 32A. As shown in FIG. 32C, shutter 356 continues to block opening 352 in second slide 350 until lever arm 356B abuts the wall of section 306 of housing 302 pushing lever arm 356B toward second slide 350 as explained above. At such time that lever arm 356B is pushed against second slide 350, shutter blade 356A is moved to an open position so that opening 352 in second slide 350 is no longer blocked. At this point, opening 352 in second slide 350 is aligned with opening 329A in divider 329 and dispensing chute 370 as shown in FIG. 32A in the dispensing position.

As can be seen in FIG. 32C, as first slide 340 is moved in direction 340Y and second slide 350 is moved in direction 350X, unit of medication $M_2$ is pushed out of opening 352 in second slide 350. In particular, as angle side 344B of first slide 340 contacts unit of medication $M_2$, unit of medication $M_2$ is pushed up front ramped surface 354 of second slide 350 and out of opening 352 in second slide 350. The angled shapes of angle side 344B of first slide 340 and front ramped surface 354 of second slide 350 facilitate movement of unit of medication $M_2$ upward and out of the opening 352 in second slide 350 without crushing or damaging unit of medication $M_2$ or jamming dispenser device 300 during operation. In this manner, unit of medication $M_2$ is pushed out of opening 352 in second slide 350 and into opening 342 in first slide 340 to wait for another dispensing opportunity.

The embodiments of the present disclosure shown in the drawings and described above are exemplary of numerous embodiments that can be made within the scope of the following claims. It is contemplated that the configurations for the devices, systems and methods for point of use medication control in the out-patient setting can comprise numerous configurations other then those specifically disclosed. Thus, it is intended that the scope of the patent issuing herefrom will only be limited by the scope of the pending claims.

What is claimed is:

1. A dispenser device for controlling dispensing of medication, the dispenser device comprising:
   a housing for storing units of medication;
   a dispensing well within the housing, the dispensing well having an opening therein to permit removal of units of medication therefrom;
   a first slide having an opening therein that is configured to funnel a unit of medication toward the opening in the dispensing well; and
   a second slide disposed between the opening in the dispensing well and the first slide, the second slide having an opening therein that is alignable with the opening in the dispensing well and the opening in the first slide;
   the opening in the first slide being configured to funnel a unit of medication to the opening of the second slide and the second slide configured to funnel the unit of medication to the opening in the dispensing well upon movement of the second slide into a position that is aligned with the opening in the dispensing well; and
   a fill door that can be opened to permit filling of the dispensing well and closed to deny access into the dispensing well therethrough.

2. The device of claim 1, wherein the dispensing well comprises a ramped surface on either side of the first slide.

3. The device of claim 1, further comprising a diverter shield disposed within the dispensing well above the first and second slides, the diverter shield configured to divert units of medication that reside above the diverter shield and first and second slides to either side of the first slide.

4. The device of claim 3, wherein the diverter shield is configured to be angled downward.

5. The device of claim 1, further comprising a tamper switch in communication with the fill door.

6. The device of claim 1, wherein the fill door comprises latches that can be engaged to lock the fill door in a closed position.

7. The device of claim 6, wherein the dispensing well comprises a rack and pinion therein with the rack being movable in transverse directions to engage with the latches of the fill door to lock the fill door and to disengage the latches of the fill door to unlock the fill door.

8. The device of claim 1, further comprising an optical detector in communication with the dispensing well.

9. The device of claim 1, wherein the opening in the first slide is configured to receive units of medication as they are oriented in a lengthwise direction to align and drop the unit of medication into the opening in the second slide.

10. The device of claim 1, wherein the first slide comprises sides that define the opening therein, the sides being angled to funnel and orient the units of medication for feeding to the opening in the second slide and to prevent jamming.

11. The device of claim 10, wherein the second slide comprises sides that define the opening therein, the sides being configured to provide a ramped surface that works in cooperation with the angled sides of the first slide to funnel and orient the units of medication for feeding to the opening in the dispensing well and to prevent jamming.

12. The device of claim 1, wherein the first slide is movable in a lateral direction.

13. The device of claim 1, wherein the second slide comprises sides that define the opening therein, the sides being configured to provide a ramped surface to funnel and orient the units of medication for feeding to the opening in the dispensing well and to prevent jamming.

14. The device of claim 1, further comprising a shutter disposed between the second slide and the dispensing well, the shutter being movable from a closed position with the opening of the second slide covered by the shutter and an open position where the opening of the second slide is not obstructed by the shutter to permit units of medication to pass through the opening in the second slide toward the opening in the dispensing well.

15. The device of claim 1, wherein the second slide is movable in a lateral direction.

16. The device of claim 1, wherein the first slide and second slide are movable in lateral directions to facilitate dispensing of a unit of medication.

17. The device of claim 16, wherein the first slide moves in a direction counter to the direction in which the second slide moves.

18. The device of claim 16, wherein the first slide and second slide are movable a distance of less than about 1.5 times the length of the unit of medication being dispensed.

19. The device of claim 16, wherein the openings of the first slide and the second slide are self-clearing through the lateral movement of the first slide and the second slide.

20. The device of claim 1, further comprising a dispensing chute disposed between the second slide and the opening in the dispensing well, the opening of the second slide being alignable with the dispensing chute and the opening in the dispensing well to provide a unit of medication for dispensing.

21. The device of claim 1, further comprising a dispensing door that closes the opening in the dispensing well.

22. The device of claim 21, wherein the dispensing door is retractable to dispense a unit of medication from the dispensing well.

23. The device of claim 22, wherein the dispensing door is manually retractable.

24. The device of claim 1, further comprising a controller operatively connected to the housing, wherein the controller operates the first slide and the second slide to dispense a unit of medication to the opening in the dispensing well.

25. The device of claim 24, further comprising an electronic communication device for connecting the controller to a remote facility.

26. The device according to claim 1, wherein the electronic communication device comprises a wireless platform.

27. The device of claim 24, further comprising an identification verification device for controlling access to the system.

28. The device according to claim 27, wherein the identification verification device comprises a biometric identification fingerprint system.

29. The device according to claim 24, further comprising a location determination device for determining the location of the dispenser.

30. The device according to claim 29, wherein the location determination device comprises an integrated Global Positioning System (GPS) receiver.

31. A system for controlling dispensing of medication, the system comprising:

a dispenser device configured for holding and delivering units of medication, the dispenser device comprising:
  a housing for storing units of medication;
  a dispensing well within the housing, the dispensing well having an opening therein to permit removal of units of medication therefrom;
  a first slide having an opening therein that is configured to funnel a unit of medication toward the opening in the dispensing well; and
  a second slide disposed between the opening in the dispensing well and the first slide, the second slide having an opening therein that is alignable with the opening in the dispensing well and the opening in the first slide; and
  the opening in the first slide being configured to funnel a unit of medication to the opening of the second slide and the second slide configured to funnel the unit of medication to the opening in the dispensing well upon movement of the second slide into a position that is aligned with the opening in the dispensing well;
a controller operatively connected to the dispenser device, wherein the controller operates the first slide and the second slide to dispense a unit of medication to the opening in the dispensing well;
an electronic communication device for connecting the controller to a remote facility; and
an identification verification device for controlling access to the system.

32. The system according to claim 31, wherein the controller is programmable with a medication dispensing program which comprises a data store comprising the predetermined time to operate the dispenser.

33. The system according to claim 32, wherein the data store further comprises at least one of the name of the at least one medication, patient data and a patient compliance schedule.

34. The system according to claim 32, wherein the controller is programmable to connect to a predetermined Internet Service Provider through the electronic communication device in order to transmit patient data and obtain a patient registration.

35. The system according to claim 34, wherein the controller is programmable to transmit an order requesting a refill of the at least one medication or the dispenser containing the at least one medication when the system is connected to the predetermined Internet Service Provider.

36. The system according to claim 32, wherein the data store further comprises caregiver data and compliance notification data.

37. The system according to claim 32, wherein the data store further comprises pharmacy data, physician data, insurance data and emergency contact data.

38. The system according to claim 37, wherein the controller is programmable to connect to a predetermined Internet Service Provider through the electronic communication device in order to transmit or receive pharmacy data, physician data, insurance data and emergency contact data.

39. The system according to claim 32, wherein the controller is programmable to connect to a predetermined Internet Service Provider through the electronic communication device in order to transmit compliance schedule and compliance notification data.

40. The system according to claim 39, wherein, when the controller has been instructed that the signal has been received, the controller is operable to transmit a compliance notification.

41. The system according to claim 40, wherein when the controller is not instructed within a predetermined time frame that the signal has been received, the controller is operable to transmit a non-compliance notification to the Internet Service Provider.

42. The system according to claim 40, wherein the controller is programmable to update and transmit the caregiver data and compliance notification data when the system is connected to the predetermined Internet Service Provider.

43. The system according to claim 31, wherein the electronic communication device comprises a wireless platform.

44. The system according to claim 31, wherein the identification verification device comprises a biometric identification fingerprint system.

45. The system according to claim 31, further comprising a location determination device for determining the location of the dispenser.

46. The system according to claim 40, wherein the location determination device comprises an integrated Global Positioning System (GPS) receiver.

47. The system according to claim 31, further comprising a lockout for disabling functionality of the system based upon a predetermined criteria.

48. The system according to claim 47, wherein the lockout comprises a breath sensor for determining a breath alcohol level and the predetermined criteria comprises a maximum breath alcohol level.

49. The system according to claim 47, wherein the lockout comprises an interactive cognitive test and the predetermined criteria comprises a minimum cognitive level.

50. A method for controlling dispensing of medication, the method comprising:
  providing a dispenser device configured for holding and delivering a unit of medication, the dispenser device comprising:
    a housing for storing units of medication;
    a dispensing well within the housing, the dispensing well having an opening therein to permit removal of units of medication therefrom;
    a first slide having an opening therein that is configured to funnel a unit of medication toward the opening in the dispensing well; and
    a second slide disposed between the opening in the dispensing well and the first slide, the second slide having an opening therein that is alignable with the opening in the dispensing well and the opening in the first slide;
    a shutter disposed between the second slide and the dispensing well; and
    the opening in the first slide being configured to funnel a unit of medication to the opening of the second slide and the second slide configured to funnel the unit of medication to the opening in the dispensing well upon movement of the second slide into a position that is aligned with the opening in the dispensing well;
  holding at least one unit of medication within the dispenser device;
  dispensing a unit of medication for the patient by moving the second slide to a receiving position until a unit of medication resides in the opening of the second slide and moving the second slide to a dispensing position where the opening in the second slide is aligned with the opening in the dispensing well; and
  confirming removal of the unit of medication from dispenser device.

51. The method according to claim 50, wherein the step of dispensing a unit of medication further comprises moving the first slide in lateral directions such that the opening in the first slide is alignable with the opening of the second slide when the second slide is in the receiving position and the first slide cover the opening of the second slide with the second slide is in the dispensing position.

52. The method according to claim 51, wherein the step of dispensing a unit of medication further comprises moving both the first slide and second slide in lateral directions to facilitate dispensing of a unit of medication.

53. The method according to claim 51, wherein the step of dispensing a unit of medication further comprises moving the second slide in lateral directions to facilitate dispensing of a unit of medication.

54. The method according to claim 50, further comprising moving the shutter between a closed position with the opening of the second slide covered by the shutter when the second slide is in the receiving position and an open position where the opening of the second slide is not obstructed by the shutter when the second slide is in the dispensing position to permit units of medication to pass through the opening in the second slide toward the opening in the dispensing well.

55. The method according to claim 50, further comprising confirming identification of the patient before dispensing a unit of medication for the patient.

\* \* \* \* \*